United States Patent
Houser et al.

(10) Patent No.: US 9,192,428 B2
(45) Date of Patent: Nov. 24, 2015

(54) SURGICAL INSTRUMENT WITH MODULAR CLAMP PAD

(75) Inventors: Kevin L. Houser, Cincinnati, OH (US); Wells D. Haberstich, Loveland, OH (US); Matthew C. Miller, Cincinnati, OH (US); Daniel W. Price, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/274,830

(22) Filed: Oct. 17, 2011

(65) Prior Publication Data

US 2012/0116433 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 17/32* (2006.01)
*A61B 18/14* (2006.01)
(Continued)

(52) U.S. Cl.
CPC ....... *A61B 18/1442* (2013.01); *A61B 17/00234* (2013.01); *A61B 17/320068* (2013.01); *A61B 17/320092* (2013.01); *A61B 18/00* (2013.01);
(Continued)

(58) Field of Classification Search
CPC .............. A61B 17/320092; A61B 17/320068; A61B 2017/2929; A61B 18/1445; A61B 2017/00477; A61B 18/1442; A61B 17/285

USPC ................................ 606/39, 45, 169; 601/2
See application file for complete search history.

(56) References Cited

U.S. PATENT DOCUMENTS

| | | |
|---|---|---|
| 1,754,806 A | 4/1930 | Stevenson |
| 3,297,192 A | 1/1967 | Swett |

(Continued)

FOREIGN PATENT DOCUMENTS

| | | |
|---|---|---|
| DE | 102008051866 | 10/2010 |
| DE | 102009013034 | 10/2010 |

(Continued)

OTHER PUBLICATIONS

International Search Report and Written Opinion dated Jan. 26, 2012 for Application No. PCT/US2011/059212.

(Continued)

*Primary Examiner* — Katherine M Shi
(74) *Attorney, Agent, or Firm* — Frost Brown Todd LLC

(57) ABSTRACT

An ultrasonic surgical instrument includes a transmission assembly extending from a body assembly that is configured to selectively couple to a disposable clamp arm. In some versions the clamp arm may include a tab that is insertable into a slot of an inner member such that actuation of the inner member rotates the clamp arm relative to a blade. In other versions the clamp arm may include a ball recess and the inner member may include a rod and ball. The clamp arm may be configured to snap onto the ball and rod. Alternatively, the clamp arm may include living hinges coupleable to an outer sheath and the inner member. Such living hinges may be unitarily formed with a clamp pad on the clamp arm. Further still, the clamp arm may be part of an end effector configured to couple to the transmission assembly via resilient tabs and slots.

7 Claims, 19 Drawing Sheets

(51) Int. Cl.

| | | |
|---|---|---|
| *A61B 17/00* | (2006.01) | |
| *A61B 18/00* | (2006.01) | |
| *A61B 18/04* | (2006.01) | |
| *H02J 7/00* | (2006.01) | |
| H01M 2/26 | (2006.01) | |
| H01M 2/10 | (2006.01) | |
| A61B 18/12 | (2006.01) | |
| A61B 19/00 | (2006.01) | |
| A61B 17/064 | (2006.01) | |
| A61B 17/285 | (2006.01) | |
| A61B 17/29 | (2006.01) | |

(52) U.S. Cl.
CPC ............... *A61B 18/04* (2013.01); *A61B 18/12* (2013.01); *A61B 18/14* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 19/38* (2013.01); *A61B 19/56* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 7,031,155 B2 | 4/2006 | Sauciuc et al. |
| 7,077,853 B2 | 7/2006 | Kramer et al. |

(56) References Cited

U.S. PATENT DOCUMENTS

| | | |
|---|---|---|
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0165541 A1* | 11/2002 | Whitman ................ 606/48 |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0234710 A1* | 9/2008 | Neurohr et al. .......... 606/169 |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |

(56) References Cited

U.S. PATENT DOCUMENTS

| | | |
|---|---|---|
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0077514 A1 | 3/2011 | Ulric et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2011/0247952 A1 | 10/2011 | Habach et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 21656602 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Search Report and Written Opinion dated Feb. 2, 2012for Application No. PCT/US2011/059378.
International Search Report dated Feb. 2, 2012for Application No. PCT/US2011/059354.
International Search Report dated Feb. 7, 2012for Application No. PCT/US2011/059351.
International Search Report dated Feb. 13, 2012for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012for Application No. PCT/US2011/059362.
Communication from International Searching Authority dated Feb. 2, 2012for Application No. PCT/US2011/059222.
Communication from International Searching Authority dated Jan. 24, 2012 for Application No. PCT/US2011/059215.
Communication from International Searching Authority dated Feb. 2, 2012for Application No. PCT/US2011/059378.
Machine Translation of the Abstract of German Application No. DE 102009013034.
Machine Translation of German Application No. DE 102008051866.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.

(56) References Cited

OTHER PUBLICATIONS

U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Jan. 29, 2014 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Dec. 5, 2013 for U.S. Appl. No. 13/275,495.
Office Action Non-Final dated Jan. 6, 2014 U.S. Appl. No. 13/275,514.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Restriction Requirement dated Jun. 11, 2014 for U.S. Appl. No. 13/151,512.
Office Action Final dated May 15, 2014 for U.S. Appl. No. 13/274,496.
Office Action Non-Final dated Jun. 19, 2014 for U.S. Appl. No. 13/274,507.
Office Action Final dated Jun. 12, 2014 for U.S. Appl. No. 13/274,516.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.

(56) References Cited

OTHER PUBLICATIONS

EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Non-Final, dated Aug. 14, 2014 for U.S. Appl. No. 13/151,481.
US Office Action, Notice of Allowance, dated Aug. 6, 2014 for U.S. Appl. No. 13/151,498.
US Office Action, Non-Final, dated Jul. 9, 2014 for U.S. Appl. No. 13/151,509.
US Office Action, Restriction Requirement, dated Jul. 11, 2014 for U.S. Appl. No. 13/269,780.
US Office Action, Non-Final, dated Jul. 29, 2014 for U.S. Appl. No. 13/270,667.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Jul. 9, 2014 for U.S. Appl. No. 13/270,684.
US Office Action, Non Final, dated Oct. 9, 2014 for U.S. Appl. No. 13/270,684.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
US Office Action, Notice of Allowance, dated Nov. 21, 2014 for U.S. Appl. No. 13/151,471.
US Office Action, Non-Final, dated Nov. 7, 2014 for U.S. Appl. No. 13/151,488.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Non-Final, dated Jan. 5, 2015 for U.S. Appl. No. 13/269,870.
US Office Action, Notice of Allowance, dated Dec. 17, 2014 for U.S. Appl. No. 13/270,667.
US Office Action, Non-Final, dated Dec. 16, 2014 for U.S. Appl. No. 13/270,701.
US Office Action, Notice of Allowance, dated Nov. 28, 2014 for U.S. Appl. No. 13/274,805.
US Office Action, Non-Final, dated Oct. 23, 2014 for U.S. Appl. No. 13/275,563.
US Office Action, Notice of Allowance, dated Dec. 23, 2014 for U.S. Appl. No. 13/276,687.
US Office Action, Notice of Allowance, dated Dec. 19, 2014 for U.S. Appl. No. 13/276,745.
US Office Action, Notice of Allowance, dated Dec. 8, 2014 for U.S. Appl. No. 13/277,328.
Chinese First Office Action dated Feb. 28, 2015 for Application No. CN 2011800641471.
Chinese First Office Action dated Feb. 2, 2015 for Application No. CN 2011800641490
US Office Action, Notice of Allowance, dated Jan. 21, 2015 for U.S. Appl. No. 13/274,805.

\* cited by examiner

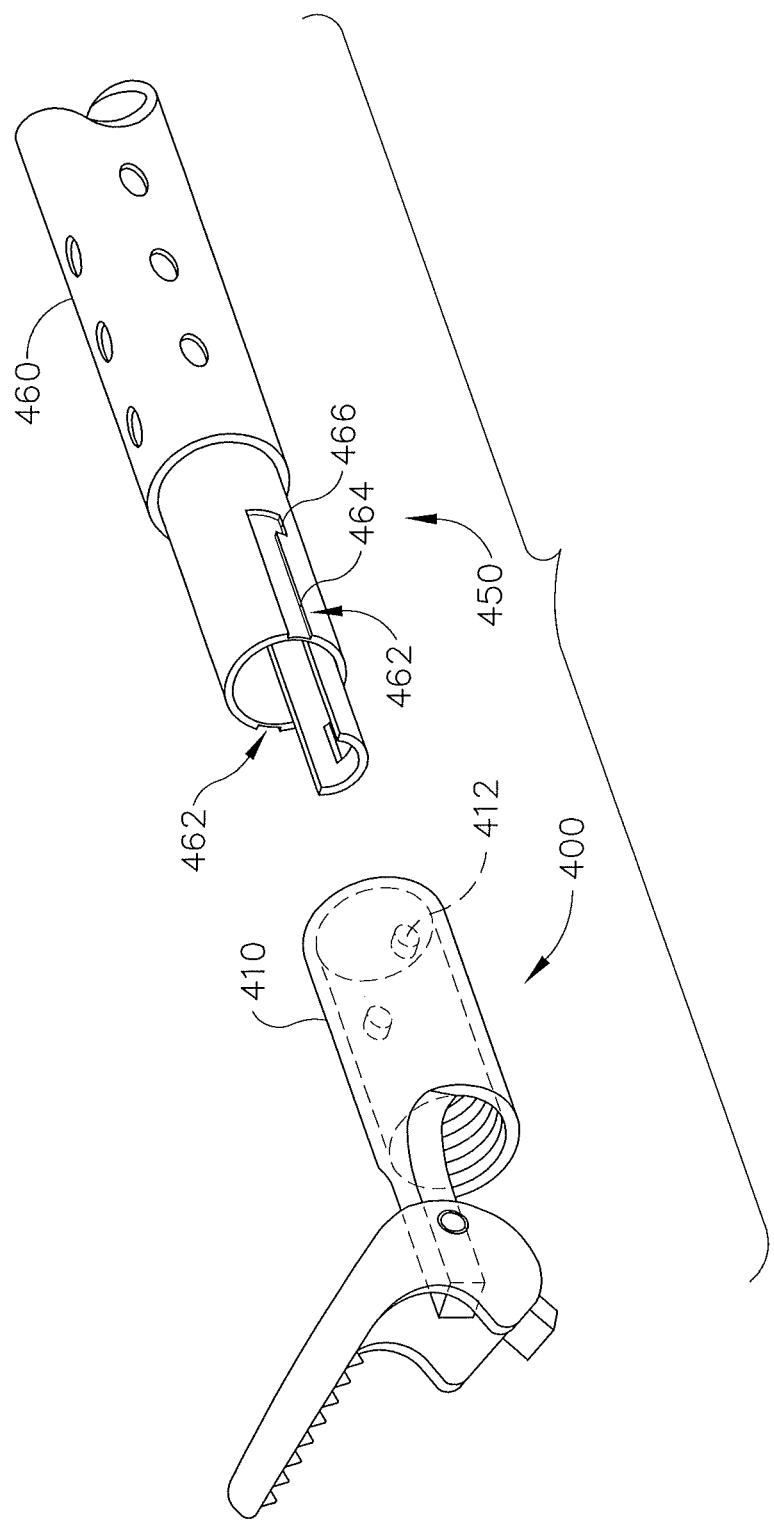

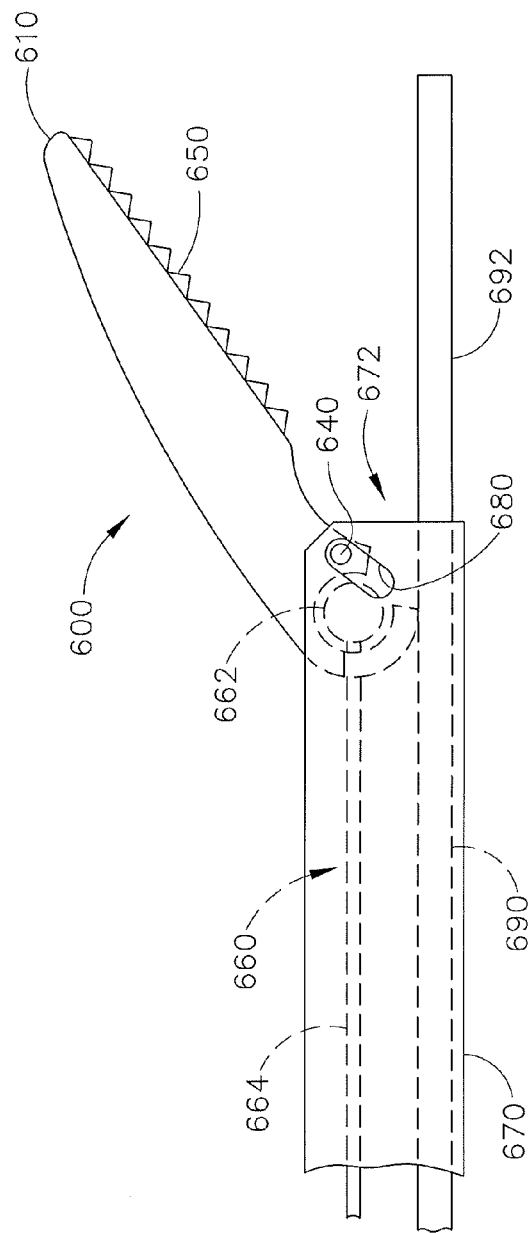
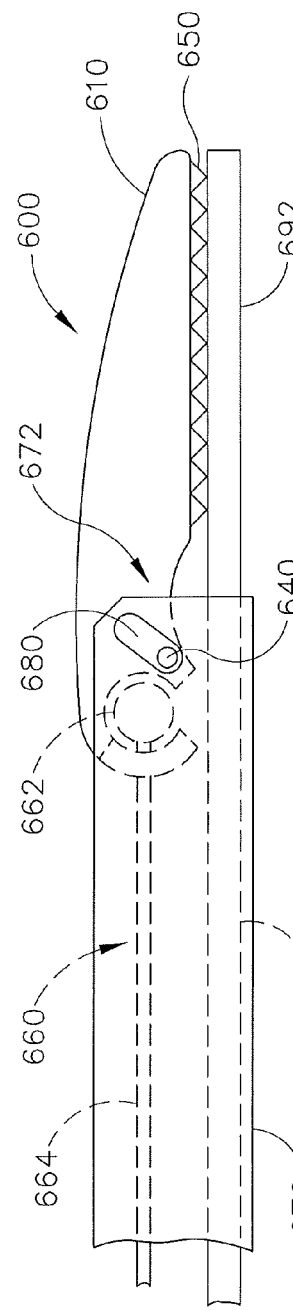

SURGICAL INSTRUMENT WITH MODULAR CLAMP PAD

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5 depicts a perspective view of an alternative tabbed clamp arm assembly and an exemplary slotted transmission assembly;

FIG. 10A depicts a side elevation view of the ball-snap clamp arm of FIG. 9 within an exemplary outer sheath having a slot and showing the clamp arm in the open position;

FIG. 10B depicts a side elevation view of the ball-snap clamp arm and the outer sheath of FIG. 10A showing the clamp arm in the closed position;

Figure 1:
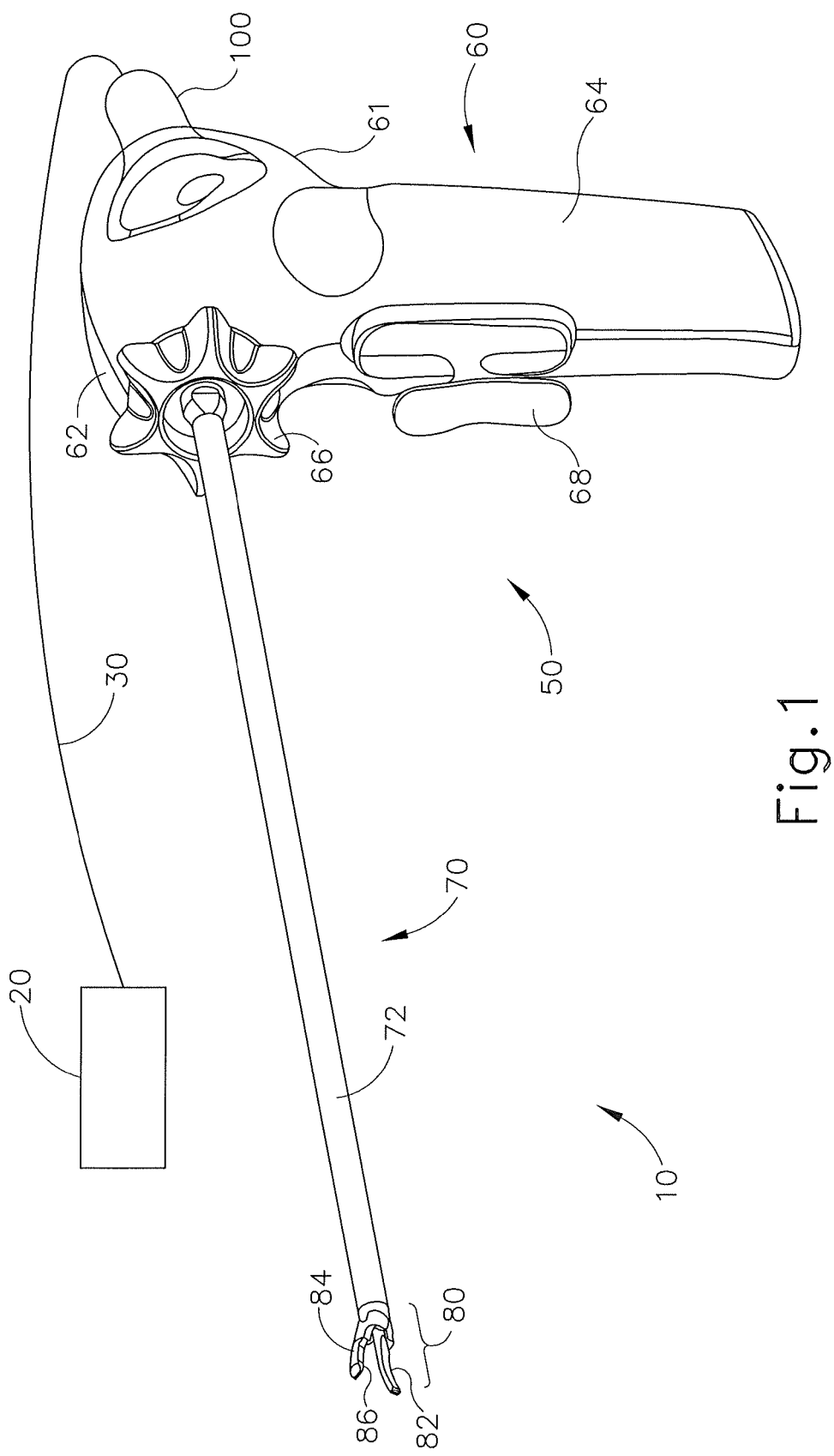
FIG. 1 depicts a perspective view of an exemplary surgical system having a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. In addition or in the alternative, generator (20) may be constructed in accordance with at least some of the teachings of in U.S. Pat. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is herein incorporated by reference.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuation member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

In some versions, transducer (100) comprises a plurality of piezoelectric elements (not shown) that are compressed between a first resonator (not shown) and a second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example. Transducer (100) further comprises electrodes, including at least one positive electrode and at least one negative electrode, that are configured to create a voltage potential across the one or more piezoelectric elements, such that the piezoelectric elements convert the electrical power into ultrasonic vibrations. When transducer (100) of the present example is activated, transducer (100) is operable to create linear oscillations or vibrations at an ultrasonic frequency (such as 55.5 kHz). When transducer (100) is coupled to transmission assembly (70), these linear oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever tissue and denature the proteins in adjacent tissue cells, thereby providing a coagulative effect with relatively little thermal spread. An electrical current may also be provided through blade (82) and clamp arm (84) to cauterize the tissue. One merely exemplary suitable ultrasonic transducer (100) is Model No. HP054, sold by Ethicon Endo-Surgery, Inc. of Cincinnati, Ohio, though it should be understood that any other suitable transducer may be used.

Transducer (100) may further be constructed in accordance with at least some of the teachings of U.S. patent application Ser. No. 13/269,883, entitled "Surgical Instrument with Clutching Slip Ring Assembly to Power Ultrasonic Transducer," filed Oct. 10, 2011, now U.S. Pat. Pub. No. 2013/0090675, published Apr. 11, 2013; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757, the disclosures of which are herein incorporated by reference.

Multi-piece handle assembly (60) of the present example comprises a mating housing portion (62) and a lower portion (64). Mating housing portion (62) defines a cavity within multi-piece handle assembly (60) and is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. In some versions toggle buttons are located on a distal surface of lower portion (64) and are operable to selectively activate transducer (100) at different operational levels using generator (20). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, only a single toggle button may be provided or more than two toggle buttons may be provided.

While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic casing (61) (such as polycarbonate or a liquid crystal polymer), ceramics, metals and/or any other suitable material as will be apparent to one of ordinary skill in the art in view of the teachings herein. Other configurations for multi-piece handle assembly (60) will also be apparent to those of ordinary skill in the art in view of the teachings herein. For instance, in some versions trigger (68) may be omitted and surgical instrument (50) may be activated by a controlled of a robotic system. In other versions, surgical instrument (50) may be activated when coupled to generator (20).

Further still, surgical instrument (50) may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Overview of an Exemplary End Effector

Figure 2A:
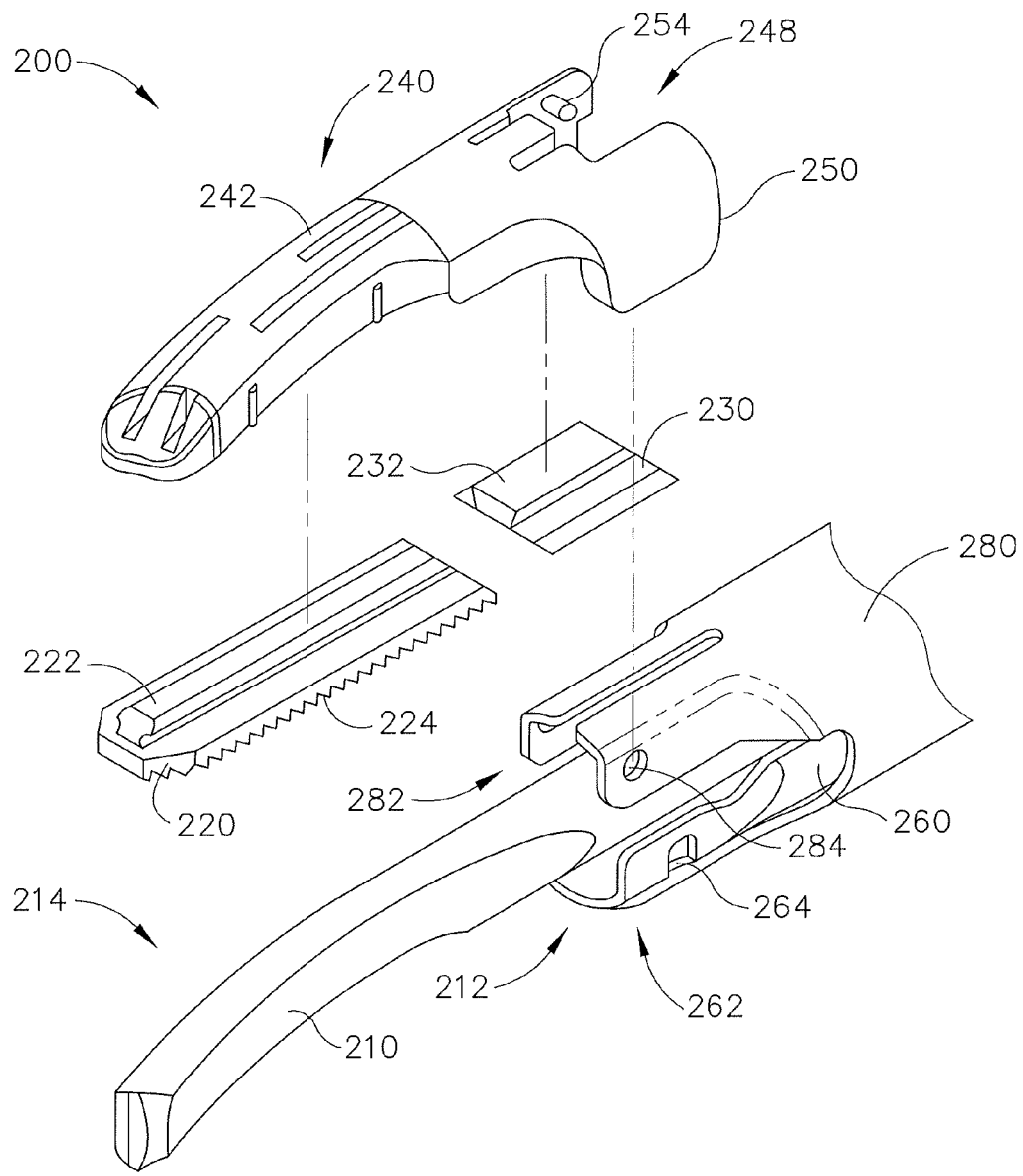
FIG. 2A depicts an exploded perspective view of an exemplary end effector shown in a closed position.
Figure 2B:
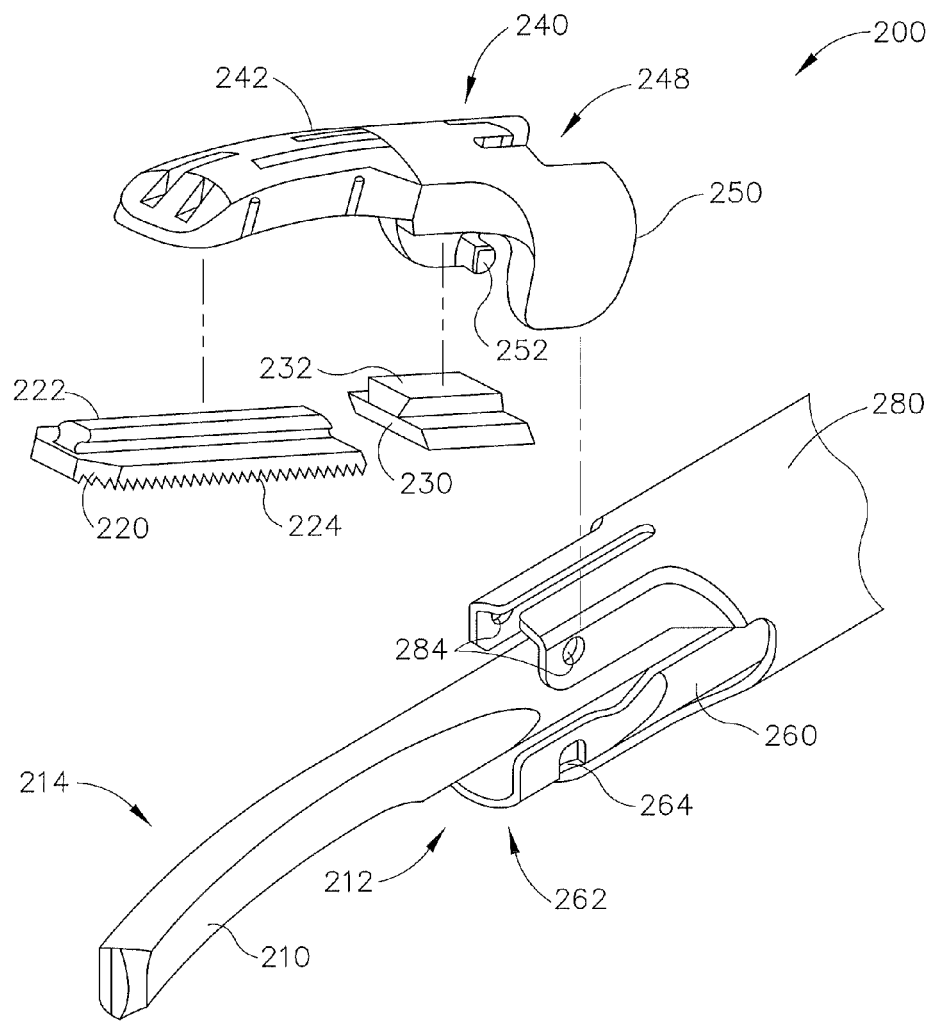
FIG. 2B depicts an exploded perspective view of the end effector of FIG. 2A shown in an open position.

FIGS. 2A-2B depict an exploded view of an exemplary end effector (200) shown in a closed position, FIG. 2A, and an open position, FIG. 2B. In the present example, end effector (200) comprises a blade (210), a distal clamp pad (220), a proximal clamp pad (230), a clamp arm (240), an inner tubular actuation member (260), and an outer sheath (280). Blade (210) may be constructed in accordance with at least some of the teachings of blade (82) described above or in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; and/or U.S. Pat. Pub. No. 2009/0143797, now U.S. Pat. No. 8,419,757, the disclosures of each are incorporated by reference herein. In the present example, blade (210) is configured to be coupled to a transducer, such as transducer (100), and to oscillate at an ultrasonic frequency. Such a coupling of blade (210) to the transducer may be via a waveguide (not shown). When tissue is secured between blade (210) and clamp arm (240), the ultrasonic oscillation of blade (210) may simultaneously sever tissue and denature the proteins in adjacent tissue cells, thereby providing a coagulative effect with relatively little thermal spread. An electrical current may also be provided through blade (210) and clamp arm (240) to cauterize the tissue. As shown, blade (210) comprises a cylindrical body portion (212) and a curved portion (214) at the distal end of blade (210). By way of example only, blade (210) comprises a solid titanium rod having a curved rectangular cuboid end. It should be understood that blade (210) may be substantially straight and/or blade (210) may have other geometries, including a conical end, a triangular prism end, a cylindrical end, a substantially planar end, a rectangular cuboid body, and/or any other geometry as will be apparent to one of ordinary skill in the art in view of the teachings herein. Further still, blade (210) may comprise materials other than titanium, including aluminium, steel, iron, composites, alloys, etc. Of course other configurations for blade (210) will be apparent to one of ordinary skill in the art in view of the teachings herein.

Distal clamp pad (220) of the present example comprises Teflon® (of E. I. du Pont de Nemours and Company of Wilmington, Del.), though distal clamp pad (220) may be formed of steel coated with Teflon® or other low-friction materials may be used as will be apparent to one of ordinary skill in the art in view of the teachings herein. Distal clamp pad (220) mounts on to clamp arm (240) via a T-shaped member (222) extending from distal clamp pad (220) and insertable into a T-shaped recess (not shown) of clamp arm (240). Distal clamp pad (220) is pivotable to a position that is substantially parallel to, and in contact with, blade (210). Accordingly, when clamp arm (240) is actuated to the closed position, shown in FIG. 2A, tissue is compressed and grasped between distal clamp pad (220) and blade (210). As illustrated, distal clamp pad (220) includes a non-smooth surface (224), such as a saw tooth-like configuration, to enhance the gripping of tissue by distal clamp pad (220). The saw tooth-like configuration, or teeth, provide traction against the movement of tissue relative to blade (210). As will be appreciated by one of ordinary skill in the art, the saw tooth-like configuration is just one example of many tissue engaging surfaces that may be used to prevent movement of the tissue relative to the movement of blade (210). Other illustrative examples include bumps, interlaced patterns, tread patterns, a bead or sand blasted surface, etc. In the example shown, distal clamp pad (220) is insertable into clamp arm (240) at a distal end and is disposed distally of proximal clamp pad (230).

Proximal clamp pad (230) comprises a substantially flat clamp pad that includes Teflon®, though proximal clamp pad (230) may be formed of steel coated with Teflon® or other low-friction materials may be used as will be apparent to one of ordinary skill in the art in view of the teachings herein. Proximal clamp pad (230) mounts on to clamp arm (240) via a dove-tailed member (232) extending from proximal clamp pad (230) and insertable into a dove-tailed recess (not shown) of clamp arm (240). Proximal clamp pad (230) is also pivotable to a position that is substantially parallel to, and in contact with, blade (210). Accordingly, when clamp arm (240) is actuated to the closed position, shown in FIG. 2A, tissue is compressed between proximal clamp pad (230) and blade (210). Of course, since distal clamp pad (220) and proximal clamp pad (230) are distinct components, the material for distal clamp pad (220) and proximal clamp pad (230) may be different. Distal clamp pad (220) and proximal clamp pad (230) may be further constructed in accordance with at least some of the teachings of U.S. Pat. Pub. No. 2006/0079874, entitled "Tissue Pad for Use with an Ultrasonic Surgical Instrument," published Apr. 13, 2006, the disclosure of which is incorporated by reference herein.

Inner tubular actuation member (260) of the present example is a hollow cylindrical member configured to actuate longitudinally within outer sheath (280) while blade (210) extends longitudinally through inner tubular actuation member (260). The proximal end of inner tubular actuation member (260) is coupled to a trigger, such as trigger (68), configured to actuate inner tubular actuation member (260) proximally when the trigger is depressed. When the trigger is released, inner tubular actuation member (260) actuates distally. Distal end (262) of inner tubular actuation member (260) comprises a pair of actuation holes (264) disposed on opposing sides of inner tubular actuation member (260) and configured to receive a pair of lower pins (252) of clamp arm (240). Accordingly, when clamp arm (240) is coupled to inner tubular actuation member (260) via actuation holes (264) and lower pins (252), the longitudinal motion of inner tubular actuation member (260) pivots clamp arm (240) about a pair of upper pins (254) of clamp arm (240). Of course other configurations and couplings for inner tubular actuation member (260) will be apparent to one of ordinary skill in the art in view of the teachings herein.

Outer sheath (280) of the present example is also a hollow cylindrical member configured to couple to a casing of a handle assembly at a proximal end (not shown) of outer sheath (280) while blade (210), inner tubular actuation member (260), and the waveguide associated with blade (210) extend longitudinally therethrough. Outer sheath (280) has a distal end (282) that includes a pair of upper holes (284) disposed on opposing sides of outer sheath (280) and configured to receive a pair of upper pins (254) of clamp arm (240). As will be apparent to one of ordinary skill in the art, upper holes (284) provide a pivot point about which clamp arm (240) is pivotable. Outer sheath (280) is further configured to be longitudinally fixed relative to inner tubular actuation member (260). Thus, when inner tubular actuation member (260) actuates longitudinally, outer sheath (280) provides a mechanical ground enabling clamp arm (240) to be pivoted. Of course, outer sheath (280) need not necessarily be fixed relative to inner tubular actuation member (260). By way of example only, inner tubular actuation member (260) may be fixed and outer sheath (280) may be actuatable or, in other versions, both inner tubular member (260) and outer sheath (280) may be actuatable. Of course other configurations for outer sheath (280) will be apparent to one of ordinary skill in the art in view of the teachings herein.

Clamp arm (240) comprises an engagement portion (242) and an attachment portion (248) proximal of engagement portion (242). Engagement portion (242) of the present example comprises a curved member having a substantially flat bottom face that includes a T-shaped recessed configured to receive T-shaped member (222) of distal clamp pad (220). Engagement portion (242) has a curvature that is substantially similar to that of blade (210) of the present example. Of course if blade (210) is straight, then engagement portion (242) may also be straight. Engagement portion (242) may further be configured to curve downwardly about the sides of blade (210) such that engagement portion (242) forms a trough into which tissue may be compressed and severed by blade (210). Attachment portion (248) comprises a body member (250), a pair of lower pins (252), and a pair of upper pins (254). Body member (250) comprises a dove-tailed recess (not shown) configured to receive dove-tailed member (232) of proximal clamp pad (230). As discussed above, lower pins (252) are insertable into actuation holes (264) of inner tubular actuation member (260) and upper pins (254) are insertable into upper holes (284) of outer sheath (280). Accordingly, when pins (252, 254) are inserted into holes (264, 284), clamp arm (240) is coupled to outer sheath (280) and inner tubular actuation member (260), and clamp arm (240) is pivotable relative to blade (210). Of course other configurations for clamp arm (240) will be apparent to one of ordinary skill in the art in view of the teachings herein. In some versions, pins (252, 254) may be separate pins insertable through holes formed in body member (250).

While one merely exemplary end effector (200) has been described herein, other end effectors may be used as well. For instance, clamp arm (240), distal clamp pad (220), proximal clamp pad (230), inner tubular actuation member (260), and/or outer sheath (280) may be omitted from end effector (200). One merely exemplary end effector omitting proximal clamp pad (230), inner tubular actuation member (260), and outer sheath (280) is described in U.S. Pat. Pub. No. 2007/0191713, entitled "Ultrasonic Device for Cutting and Coagulating," published Aug. 16, 2007, the disclosure of which is herein incorporated by reference. Another merely exemplary end effector omitting clamp arm (240), distal clamp pad (220), proximal clamp pad (230), and inner tubular actuation member (260) is described in U.S. Pat. Pub. No. 2008/0200940, entitled "Ultrasonic Device for Cutting and Coagulating," published Aug. 21, 2008, the disclosure of which is herein incorporated by reference. Still other configurations for end effector (200) will be apparent to one of ordinary skill in the art in view of the teachings herein.

III. Exemplary Modular Clamp Pad Assemblies

In some situations, it may be preferable to detach only clamp arm (84), a portion of an inner tubular actuation member, and/or a portion of outer sheath (72) from surgical instrument (50). For instance, portions of outer sheath (72), portions of inner tubular actuation member, and/or clamp arm (84) may be rendered unclean during a surgical procedure. In such instances, it may be difficult to clean and resterilized the portion of outer sheath (72), portion of inner tubular actuation member, and/or clamp arm (84) between uses. Accordingly, it may be preferable to have a disposable clamp arm assembly that may be coupled and decoupled from transmission assembly (70) of surgical instrument (50). Transmission assembly (70) and/or surgical instrument (50) may be configured to be reusable, reclaimable, and/or resterilizable. Thus, a user may discard a used clamp arm assembly, resterilize transmission assembly (70) and/or surgical instrument (50), and couple a new clamp arm assembly onto transmission assembly (70) for use in another procedure. In other situations, it may be useful to be able to change the clamp arm assembly if clamp arm (84) and/or clamp pads (86) wear out, jam, and/or are rendered inoperable or unusable. In such situations, it may be useful to be able to change the clamp arm assembly rather than transmission assemblies (70), blades (82), and/or surgical instruments (50). Of course in some versions it may be preferable to also have a detachable blade (82). Accordingly, various configurations for decoupleable clamp arm assemblies will be described below.

A. Exemplary Tabbed Clamp Arm Assembly

Figure 3:
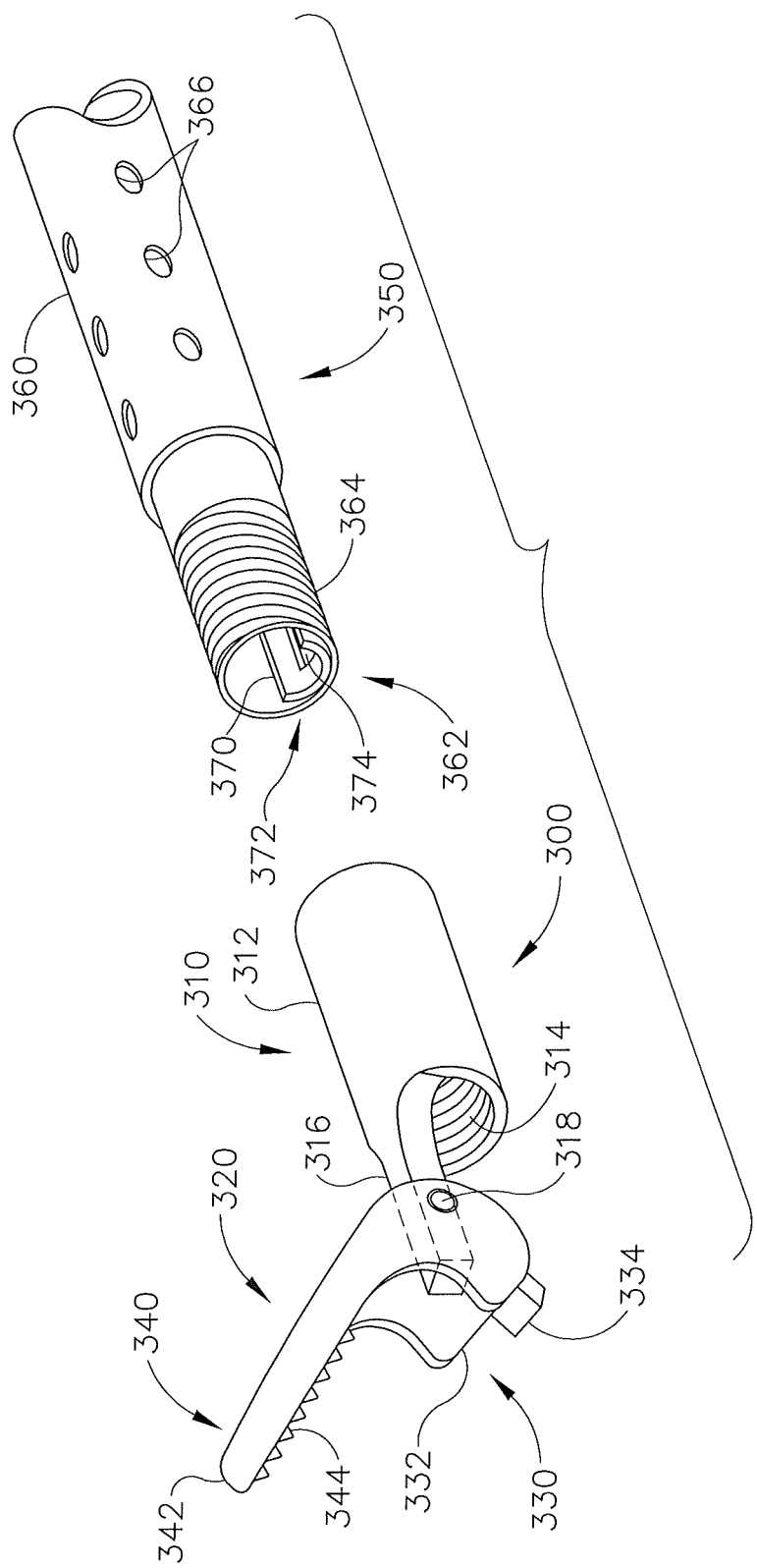
FIG. 3 depicts a perspective view of an exemplary tabbed clamp arm assembly and an exemplary threaded transmission assembly having a plurality of sterilization holes.

FIG. 3 depicts an exemplary tabbed clamp arm assembly (300) and an exemplary slotted transmission assembly (350). Transmission assembly (350) of the present example extends distally from a handle assembly, such as multi-piece handle assembly (60) described above, and comprises an outer sheath (360) and an actuator (370). It should be understood that a waveguide (not shown) and/or a blade (not shown) also extend distally from the handle assembly, but have been omitted for clarity. The waveguide and/or blade are disposed within outer sheath (360). The waveguide and/or blade may be integrated into the handle assembly and/or a transducer, such as transducer (100), or the waveguide and blade may be detachable from the handle assembly. In some versions, the blade may be selectively coupleable to the waveguide, such as blades (82, 210, 394, 692, 794, 810, 930) described herein. Merely exemplary handle assemblies, transducers, waveguides, and/or blades are disclosed in U.S. Pat. Pub. No. 2012/0116263, entitled "Gear Driven Coupling Between Ultrasonic Transducer and Waveguide in Surgical Instrument," published May 10, 2012; U.S. Pat. Pub. No. 2012/0116262, entitled "Cam Driven Coupling Between Ultrasonic Transducer and Waveguide in Surgical Instrument," published May 10, 2012; U.S. patent application Ser. No. 13/269,870, entitled "Surgical Instrument with Modular Shaft and End Effector," filed Oct. 10, 2011, now U.S. Pat. Pub. No. 2012/0116388, published May 10, 2012; U.S. patent application Ser. No. 13/269,899, entitled "Ultrasonic Surgical Instrument with Modular End Effector," filed Oct. 10, 2011, now U.S. Pat. No. 9,050,125, issued Jun. 9, 2015; U.S. patent application Ser. No. 13/269,883, entitled "Surgical Instrument with Clutching Slip Ring Assembly to Power Ultrasonic Transducer," filed Oct. 10, 2011, now U.S. Pat. Pub. No. 2013/0090675, published Apr. 11, 2013; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757, the disclosures of which are herein incorporated by reference.

Outer sheath (360) of the present example is an elongated tubular member coupled at a proximal end to the handle assembly. Outer sheath (360) comprises a distal end (362) having threading (364) and a plurality of holes (366) perpendicular to a longitudinal axis of outer sheath (360). Distal end (362) and threading (364) are configured to threadably couple to threading (314) of an outer sheath portion (310) that complements threading (364). Holes (366) extend through outer sheath (360) to provide fluid access to the interior of outer sheath (360). By way of example only, holes (366) may be disposed about the cylindrical surface of outer sheath (360) in a grid like pattern, in an offset grid pattern, randomly, or in any other manner as will be apparent to one of ordinary skill in the art in view of the teachings herein. Holes (366) permit a user to use a fluid to flush the interior of transmission assembly (350) to sterilize and/or resterilize transmission assembly (350). In some versions, an inner tubular actuation member may be disposed within outer sheath (360), such as inner tubular actuation member (780) shown in FIG. 15. Such an inner tubular actuation member may also include holes therethrough to permit fluid flow into the interior of both the inner tubular actuation member and outer sheath (360). Such holes on the inner tubular actuation member may be aligned and/or may be offset from holes (366) of outer sheath (360). Of course holes (366) are merely exemplary. Indeed, outer sheath (360) and/or the inner tubular actuation member may include longitudinal slots, circumferential slots, mesh, and/or any other form of aperture that permits fluid communication through outer sheath (360) and/or the inner tubular actuation member.

In some other versions, an exterior tube (not shown) may be provided outside of outer sheath (360). The exterior tube may also comprise holes similar to holes (366). In some versions, the exterior tube may be rotated from a first position, in which the holes of the exterior tube align with holes (366) of outer sheath (360) such that fluid may flow into outer sheath (360), to second position, in which the holes in the exterior tube are offset from holes (366) of outer sheath (360) and outer sheath (360) is substantially fluidly sealed therein. Furthermore, the exterior tube may include a key that inserts into a key slot (not shown) formed in outer sheath (360) to rotationally align the exterior tube with outer sheath (360) in the first position or the second position. Of course other alignment features such as detents, notches, etc., may be provided as well or in the alternative. Still other configurations for outer sheath (360) will be apparent to one of ordinary skill in the art in view of the teachings herein.

Actuator (370) of the present example comprises an arcuate member extending longitudinally through outer sheath (360). In the present example, actuator (370) comprises a hemi-tubular member having a slot (374) formed just proximal of a distal end (372) of actuator (370). Furthermore, actuator (370) is axially offset from the longitudinal axis of outer sheath (360), though this is merely optional. Slot (374) comprises an aperture formed through actuator (370) and is configured to receive tab (334) of clamp arm (320), described in more detail below. Actuator (370) is operable to actuate longitudinally relative to outer sheath (360) from a loading position, in which slot (374) is at a first distal location relative to distal end (362) of outer sheath (360) (shown in FIG. 4A), to a closed position in which slot (374) is in a third distal location that is closer to distal end (362) of outer sheath (360) relative to the first distal location (as shown in FIG. 4C). Actuator (370) may also be actuated to an open position that is located between the loading position and the closed position (shown in FIG. 4B). It should be understood that such positions for actuator are merely exemplary, and actuator (370) may be operable to actuate to a variety of positions distal and/or proximal to distal end (362) of outer sheath (360). In some versions, actuator (370) may comprise a tubular member, such as inner tubular actuation member (780) shown in FIG. 15, that is coaxial with outer sheath (360). In other versions, actuator (370) may simply comprise a planar member. Actuator (370) and/or slot (374) may further comprise a retention feature (not shown) for coupling to tab (334). For instance, resiliently biased locks, detents, T-shaped slots for receiving a T-shaped tab, other narrowing slots, snaps, clips, clamps, etc. may be provided. Still other configurations for actuator (370) and/or slot (374) will be apparent to one of ordinary skill in the art in view of the teachings herein.

Clamp arm assembly (300) of the present example comprises an outer sheath portion (310) and a clamp arm (320) pivotably coupled to outer sheath portion (310). Outer sheath portion (310) comprises a tubular member (312) having a distal rod (316) extending from a distal end of tubular member (312). Tubular member (312) includes threading (314) complementary to threading (364) of outer sheath (360), and tubular member (312) is configured to threadably couple onto distal end (362) of outer sheath (360). In some versions tubular member (312) may be configured to threadably insert into outer sheath (360). Of course alternative couplings for tubular member (312) to outer sheath (360) will be apparent to one of ordinary skill in the art in view of the teachings herein. By way of example only, adhesives, set screws, interference fittings, clips, clamps, snaps, resiliently biased locks, etc. may be provided. Rod (316) extends distally from tubular member (312) and includes a pair of pins (318) extending outwardly from rod (316). Pins (318) are insertable into clamp arm (320) such that clamp arm (320) is pivotable relative to outer sheath portion (310).

Clamp arm (320) comprises an actuation portion (330) and a clamp portion (340). Actuation portion (330) includes a tabbed member (332) having a tab (334) extending downwardly from tabbed member (332). Tabbed member (332) of the present example includes a cylindrical tube, though it should be understood that tabbed member (332) may have alternative forms, including a rectangular tube, an ovular member, a frame-like member, etc. Tab (334) comprises a rectangular projection from tabbed member (332) that is configured to insert into slot (374) of actuator (370) when actuator (370) is extended into the open position. For instance, actuator (370) and/or tab (334) may be made of a resilient material such that one or both of actuator (370) and/or tab (334) flex to allow tab (334) to enter slot (374). In some versions tab (334) and/or actuator (370) may include a camming surface (not shown) to assist the insertion of tab (334) into slot (374). Tab (334) is further sized to permit actuator (370) to actuate clamp arm (320) from an open position, in which clamp portion (340) forms an angle to the blade (not shown), to a closed position, in which clamp portion (340) and/or a clamp pad (344), described below, is parallel to and/or compressed against the blade. In some versions, tab (334) may be T-shaped and slot (374) may comprise a T-shaped slot that permits the top of the T of tab (334) to enter the top of the T of slot (374) during loading. During operation, the base of the T of tab (334) is retained within the T-shaped slot (374) by the top of the T of tab (334). Of course other configurations for tab (334) and slot (374) will be apparent to one of ordinary skill in the art in view of the teachings herein. Moreover, other configurations for actuation portion (330) may be used. For instance, tab (334) may be coupled to actuator (370) via resiliently biased pins in actuator (370) and/or tab (334). In other versions, tab (334) and/or actuator (370) may include a magnet to magnetically couple tab (334) and actuator (370). Further still, actuator (370) may include a resilient snap-in feature to couple tab (334) to actuator. Still other versions will be apparent to one of ordinary skill in the art in view of the teachings herein.

Clamp portion (340) comprises an arm (342) and, in some versions, a clamp pad (344). Arm (342) and clamp pad (344) of the present example are configured substantially in accordance with clamp arm (240) and distal clamp pad (220) described above and shown in FIGS. 2A-2B. It should be understood that a proximal clamp pad (230) may also be included with clamp portion (340). Of course clamp portion (340) may alternatively or further be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757, the disclosures of which are herein incorporated by reference.

Figure 4A:
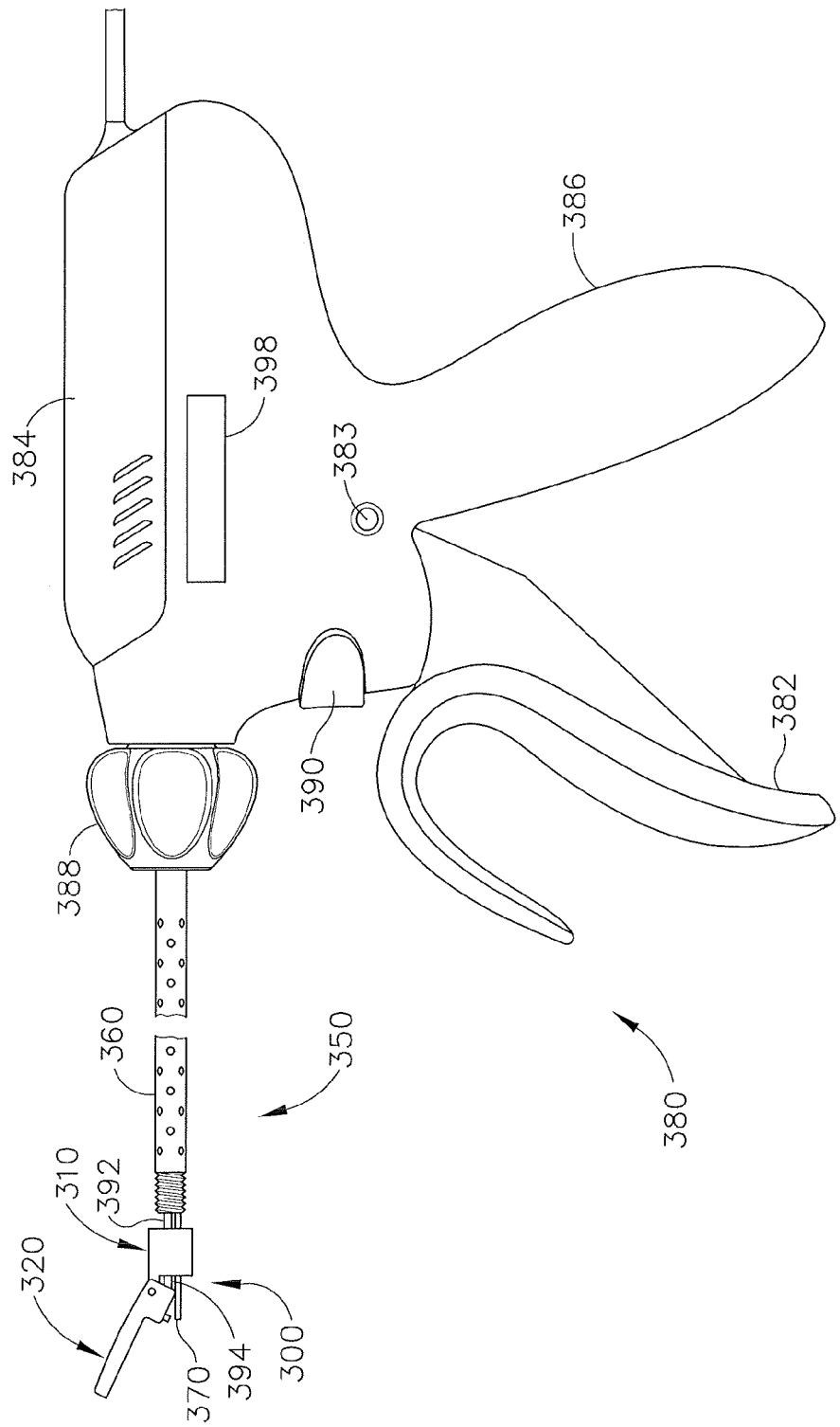
FIG. 4A depicts a side elevation view of an exemplary handle assembly comprising the transmission assembly of FIG. 3 and the clamp arm assembly of FIG. 3 showing a trigger in the loading position.
Figure 4B:
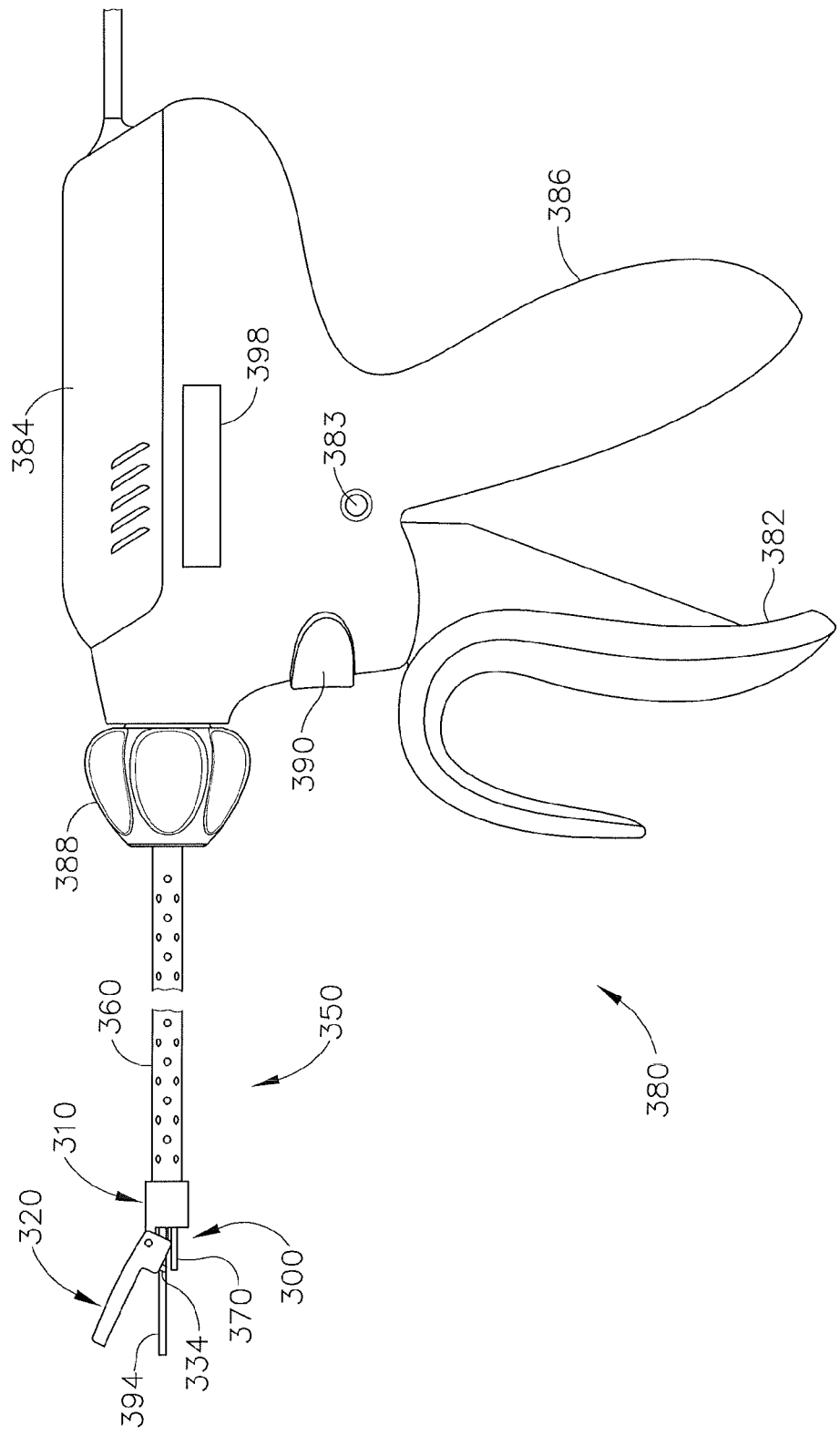
FIG. 4B depicts a side elevation view of the handle assembly of FIG. 4A with the tabbed clamp arm assembly coupled to the transmission assembly and the trigger and the clamp arm in the open position.
Figure 4C:
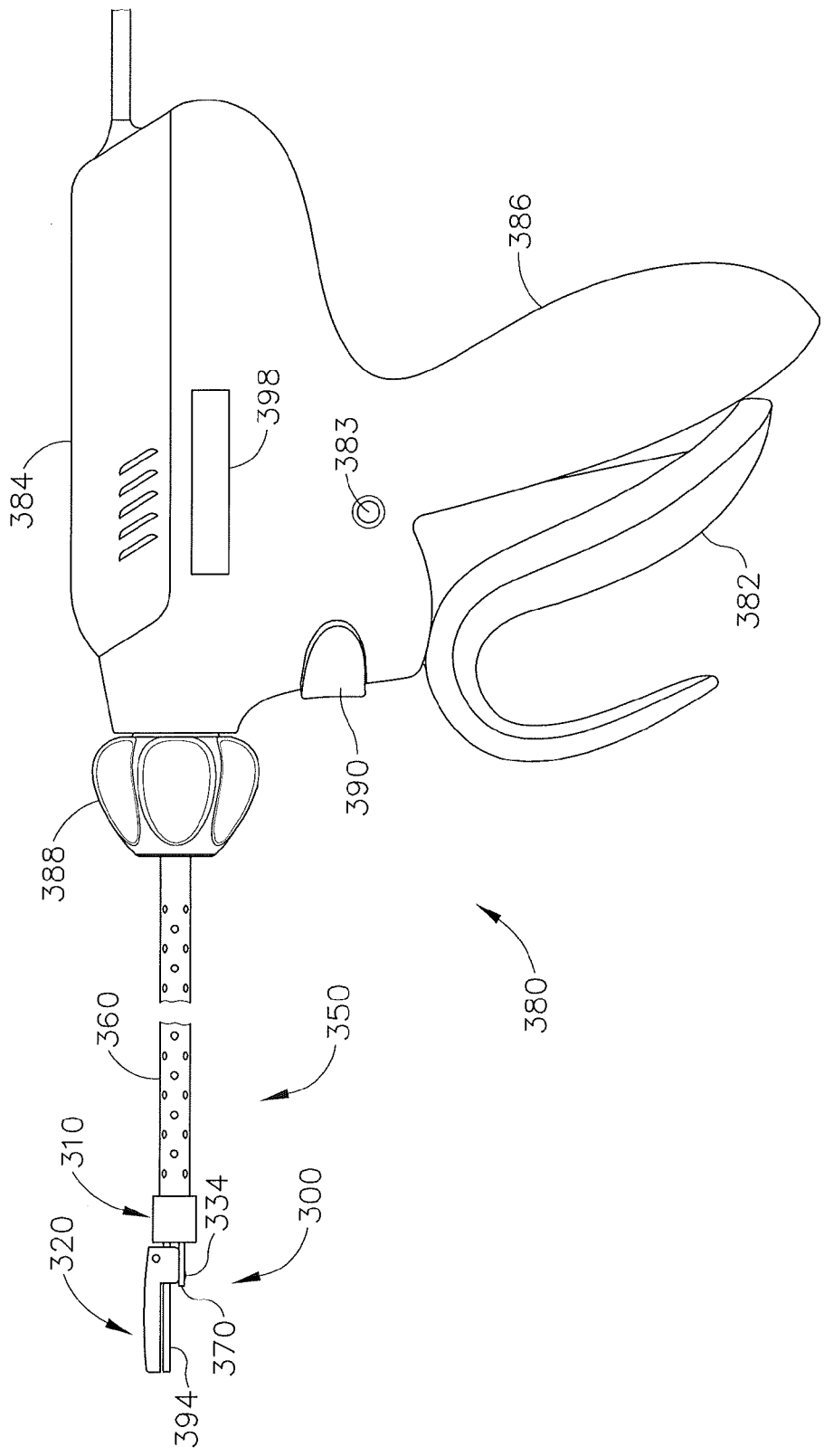
FIG. 4C depicts a side elevation view of the handle assembly of FIG. 4B showing the trigger and the clamp arm in the closed position.

Referring now to FIG. 4A, transmission assembly (350) is coupled to a handle assembly (380) comprising a trigger (382), a transducer (384), a casing (386), a rotation knob (388), a toggle button (390), a waveguide (392), and a blade (394). Handle assembly (380), including trigger (382), transducer (384), casing (386), rotation knob (388), toggle button (390), waveguide (392), and blade (394), of the present example may be configured in accordance with at least some of the teachings of U.S. Pat. Pub. No. 2012/0116263, entitled "Gear Driven Coupling Between Ultrasonic Transducer and Waveguide in Surgical Instrument," published May 10, 2012; U.S. Pat. Pub. No. 2012/0116262, entitled "Cam Driven Coupling Between Ultrasonic Transducer and Waveguide in Surgical Instrument," published May 10, 2012; U.S. patent application Ser. No. 13/269,870, entitled "Surgical Instrument with Modular Shaft and End Effector," filed Oct. 10, 2011, now U.S. Pat. Pub. No. 2012/0116388, published May 10, 2012; U.S. patent application Ser. No. 13/269,899, entitled "Ultrasonic Surgical Instrument with Modular End Effector," filed Oct. 10, 2011, now U.S. Pat. No. 9,050,125, issued Jun. 9, 2015; U.S. patent application Ser. No. 13/269,883, entitled "Surgical Instrument with Clutching Slip Ring Assembly to Power Ultrasonic Transducer," filed Oct. 10, 2011, now U.S. Pat. Pub. No. 2013/0090675, published Apr. 11, 2013; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757.

In the present example, trigger (382) is coupled to an actuation assembly (398) that is further coupled to actuator (370). Trigger (382) and actuation assembly (398) may be constructed in accordance with at least some of the teachings of U.S. Pat. Pub. No. 2006/0079874, entitled, "Tissue Pad for Use With an Ultrasonic Surgical Instrument," published Apr. 13, 2006, the disclosure of which is incorporated by reference herein. When trigger (382) is pivoted distally (FIG. 4A), actuation assembly (398) actuates actuator (370) distally into the loading position, as described above. In the present example, a spring loaded locking assembly (383) prevents the user from inadvertently actuating trigger (382) distally to the loading position unless user interaction is provided (e.g., pressing a release button). In the present example locking assembly (383) comprises a safety button coupled to a spring biased lever arm that prevents trigger (382) from pivoting distally. Of course other locking assemblies will be apparent to one of ordinary skill in the art in view of the teachings herein. From the loading position, trigger (382) is proximally pivotable to an open position (FIG. 4B) in which actuation assembly (398) actuates actuator (370) proximally from the loading position. When trigger (382) is actuated from the loading position to the open position, spring loaded locking assembly (383) engages to prevent trigger (382) from pivoting back to the loading position Finally, when trigger (382) is further pivoted proximally (FIG. 4C), actuation assembly (398) actuates actuator (370) proximally to the closed position. Still further configurations for trigger (382) and/or handle assembly (380) will be apparent to one of ordinary skill in the art in view of the teachings herein. For instance, it should be understood that the loading position is merely optional, and, in some versions, trigger (382) may simply be pivoted to the open position to substantially extend actuator (370) and then insert tab (334) of clamp arm (320) into slot (374) of actuator (370).

To assemble clamp arm assembly (300) with transmission assembly (350), the user initially disengages the locking assembly (383) and extends actuator (370) to the loading position via trigger (382) of handle assembly (380) shown in FIG. 4A. With actuator (370) extended, the user inserts blade (394) through clamp arm assembly (300) and screws clamp arm assembly (300) onto transmission assembly (350) via threading (314, 364). At this time, tab (334) is also inserted into slot (374). Trigger (382) is then pivoted proximally toward the open position, shown in FIG. 4B. It should be understood that locking assembly (383) reengages to prevent trigger (382) from pivoting back to the loading position. With tab (334) within slot (374), the user may then use the surgical instrument to actuate clamp arm (320). For instance, as shown in FIG. 4C, the user may actuate trigger (382) proximally to the closed position to clamp arm (320) against blade (394). Accordingly, when tissue is secured between blade (394) and clamp arm (320) and transducer (384) is activated, the ultrasonic oscillation of blade (394) may simultaneously sever tissue and denature the proteins in adjacent tissue cells, thereby providing a coagulative effect with relatively little thermal spread.

In one alternative version, the loading position for actuator (370) may be located proximal of distal end (362) of outer sheath (360). In such a configuration, trigger (382) is configured to have an alternate loading position in which trigger (382) is pivoted to a position proximal of the closed position. With trigger (382) pivoted to this alternate loading position, actuator (370) is retracted proximally relative to the position of actuator (370) in the closed position. With actuator (370) in this alternate loading position, clamp arm assembly (300) may be coupled to transmission assembly (350) via threading (314, 364). In this example, blade (394) is initially decoupled from transmission assembly (350) while clamp arm assembly (300) is coupled to transmission assembly (350). Clamp arm (320) is then able to be pivoted downwardly past the closed position such that tab (334) may be inserted into slot (374). Once clamp arm assembly (300) is coupled to transmission assembly (350), the user then pivots trigger (382) distally back to the closed position and/or the open position. The user may then attach blade (394) and use the surgical device.

Referring back to the present example, to remove clamp arm assembly (300) from transmission assembly (350), the user initially actuates actuator (370) to the open position via trigger (382). The user then disengages locking assembly (383) and actuates actuator (370) to the loading position shown in FIG. 4A. The user then grasps clamp arm (320) to lift tab (334) out of slot (374). In some versions with locking or retention features, a button, slider, and/or separate tool may be used to release tab (334) from slot (374). With tab (334) removed from slot (374), the user then unthreads clamp arm assembly (300) from transmission assembly (350). Clamp arm assembly (300) may then be disposed of, cleaned, and/or reclaimed. In the present example, clamp arm assembly (300) is provided as a disposable unit. Transmission assembly (350) and the remainder of the surgical instrument may also be disposed of, cleaned, and/or reclaimed. In the present example, the user may flush sterilizing fluids through holes (366) of outer sheath (360) to resterilize transmission assembly (350) prior to using the surgical device again. A new clamp arm assembly (300) may then be attached to transmission assembly (350) and used.

FIG. 5 depicts an exemplary alternative tabbed clamp arm assembly (400) and an exemplary alternative slotted transmission assembly (450). In the present example, clamp arm assembly (400) is configured substantially in accordance with clamp arm assembly (300), although threading (314) has been omitted and a pair of bayonet pins (412) (shown in phantom) extend inwardly from an inner surface of an outer sheath portion (410). It should be understood that bayonet pins (412) may alternatively extend outwardly from outer sheath portion (410). Of course a single bayonet pin (412) or more than two bayonet pins (412) may be used as well. Still other configurations for outer sheath portion (410) will be apparent to one of ordinary skill in the art in view of the teachings herein.

Transmission assembly (450) is configured substantially in accordance with transmission assembly (350), though threading (364) of outer sheath (360) has been omitted. Instead, outer sheath (460) includes a pair of longitudinally extending bayonet slots (462) configured to receive bayonet pins (412). By way of example only, bayonet slots (462) are L-shaped slots having an entrance portion (464) and a lock portion (466). In the present example, bayonet slots (462) are recesses formed in the surface of outer sheath (460), but do not extend through outer sheath (460). This is merely optional, and in some versions bayonet slots (462) extend through outer sheath (460). In still other versions, bayonet slots (462) may be formed on the interior surface of outer sheath (460) to receive bayonet pins (412) on the exterior of outer sheath portion (410). As noted previously, bayonet slots (462) each include an entrance portion (464) and a lock portion (466). Entrance portion (464) extends proximally from a distal end of outer sheath (460). Lock portion (466) extends circumferentially from entrance portion (464) at the proximal end of entrance portion (464). In some versions, multiple lock portions (466) may extend from entrance portion (464) to accommodate a variety of depths for coupling clamp arm assembly (400). Such multiple lock portions (466) may permit additional modularity for coupling clamp arm assemblies to transmission assembly (450). Lock portion (466) may further comprise detents, snap features, resiliently biased locks, and/ or any other retention feature to retain bayonet pins (412) within lock portion (466). Alternatively, lock portion (466) may be omitted and the proximal end of entrance portion (464) may include detents, snap features, resiliently biased locks, and/or any other retention feature to retain bayonet pins (412) at the proximal end of entrance portion (464). Such retention features may help retain clamp arm assembly (400) within lock portion (466) and/or entrance portion (464) and/ or such retention features may provide tactile feedback to the user to indicate that clamp arm assembly (400) is coupled to transmission assembly (450). In yet a further alternative, bayonet slots (462) may comprise helical slots. Of course other configurations for transmission assembly (450) will be apparent to one of ordinary skill in the art in view of the teachings herein.

To assemble clamp arm assembly (400) with transmission assembly (450), the user inserts bayonet pins (412) into bayonet slots (462) until bayonet pins (412) reach the proximal end of entrance portions (464). The user then rotates clamp arm assembly (400) to rotate bayonet pins (412) into lock portions (466). Such rotation may be from zero degrees, inclusive, to 180 degrees. In versions comprising helical slots, such rotation may be up to or even greater than 360 degrees. By way of example only, a helical slot may have the clamp arm assembly (400) rotate through 1080 degrees of rotation. The user may further couple the tab to the actuator and slot to use the surgical instrument.

Figure 6:
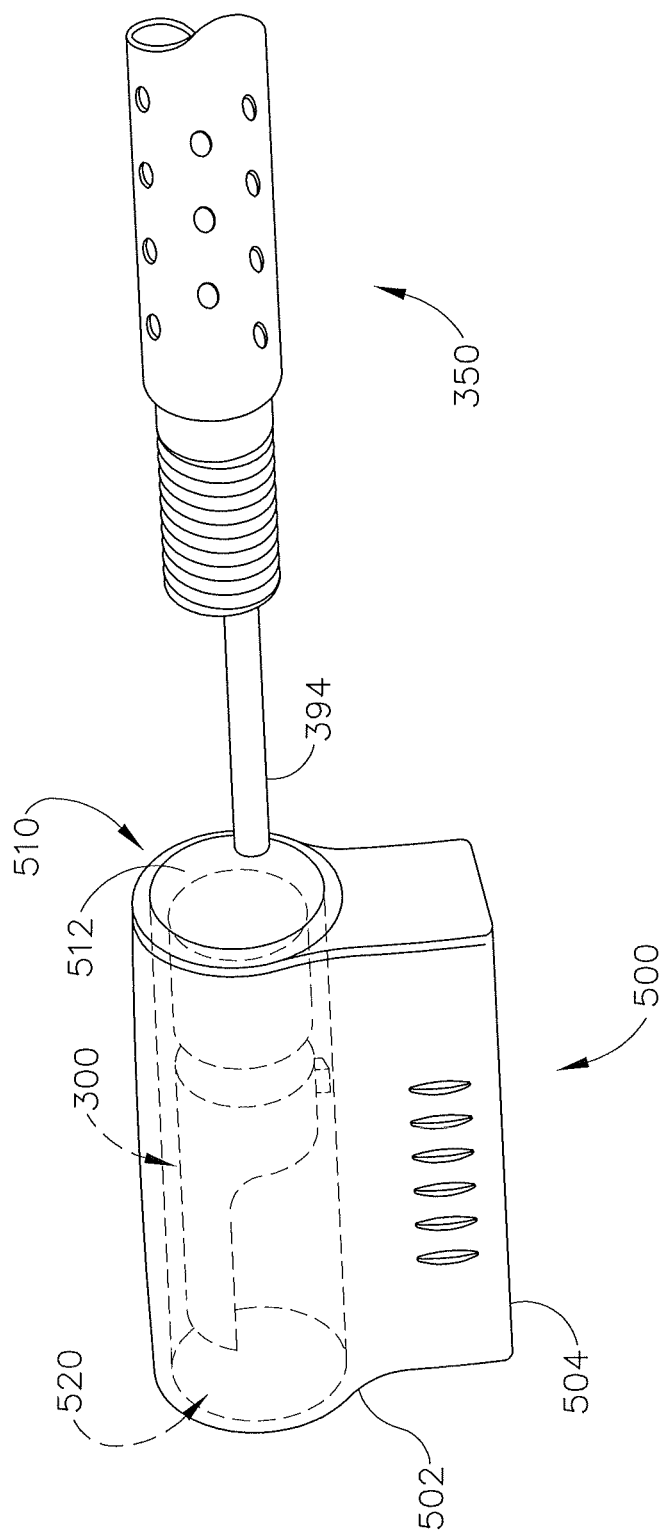
FIG. 6 depicts a perspective view of an exemplary cartridge containing the tabbed clamp arm assembly of FIG. 3.

FIG. 6 depicts a cartridge (500) that may be used for coupling a sterilized clamp arm assembly (300) to transmission assembly (350). Cartridge (500) comprises a body (502), an aperture (510) formed in body (502), and a recess (520) extending from aperture (510) and in which clamp arm assembly (300) is disposed. Body (502) may include a handle portion (504) with which a user may grasp and rotate cartridge (500) to couple clamp arm assembly (300) to transmission assembly (350). In some versions, cartridge (500) may include a fixation feature (not shown) that prevents clamp arm assembly (300) from rotating within cartridge (500). For instance, bosses, push-button brake pads, clips, clamps, snaps, resiliently biased members, etc. may be provided. A removable cover (512), such as a Tyvek® (of E. I. du Pont de Nemours and Company of Wilmington, Del.) cover, may be used to cover aperture (510) prior to coupling clamp arm assembly (300) with transmission assembly (350). In some versions, cover (512) may comprise a pierceable cover such that blade (394) may pierce through cover (512) to permit access to clamp arm assembly (300) therein. In the present example, clamp arm assembly (300) is threaded onto transmission assembly (350) by rotating cartridge (500) relative to transmission assembly (350). In other versions, such as clamp arm assembly (400) and transmission assembly (450), cartridge (500) may be rotated a quarter turn (90 degrees) relative to transmission assembly (450) to coupled clamp arm assembly (400) to transmission assembly (450). Of course other rotational angles for cartridge (500) relative to transmission assembly (350) may be used. In addition, other versions of cartridge (500) will be apparent to one of ordinary skill in the art in view of the teachings herein. It should be understood that cartridge (500) may be pulled directly from sterile packaging to couple clamp arm assembly (300) with transmission assembly (350) without compromising the sterility of clamp arm assembly (300) through the act of coupling. Of course clamp arm assembly (300) may still be coupled with transmission assembly (350) without compromising sterility, even in the absence of cartridge (500). Moreover, while the present example depicts clamp arm assembly (300) in a closed position for assembly, other configurations and/or orientations for clamp arm assembly (300) may be used with cartridge (500) as will be apparent to one of ordinary skill in the art in view of the teachings herein.

B. Exemplary Ball-Snap Clamp Arm

Figure 8:
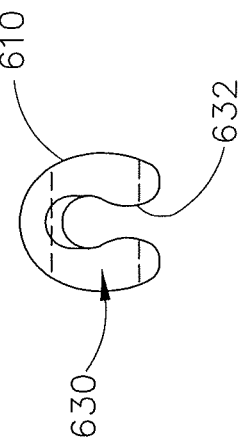
FIG. 8 depicts a rear elevation view of the ball-snap clamp arm of FIG. 7 showing a pair of detents.
Figure 7:
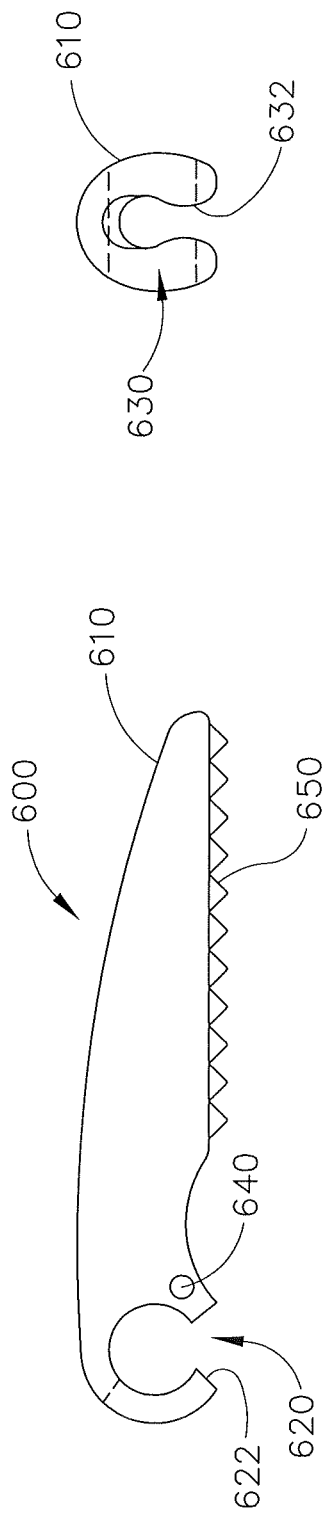
FIG. 7 depicts a side elevation view of an exemplary ball-snap clamp arm.
Figure 9:
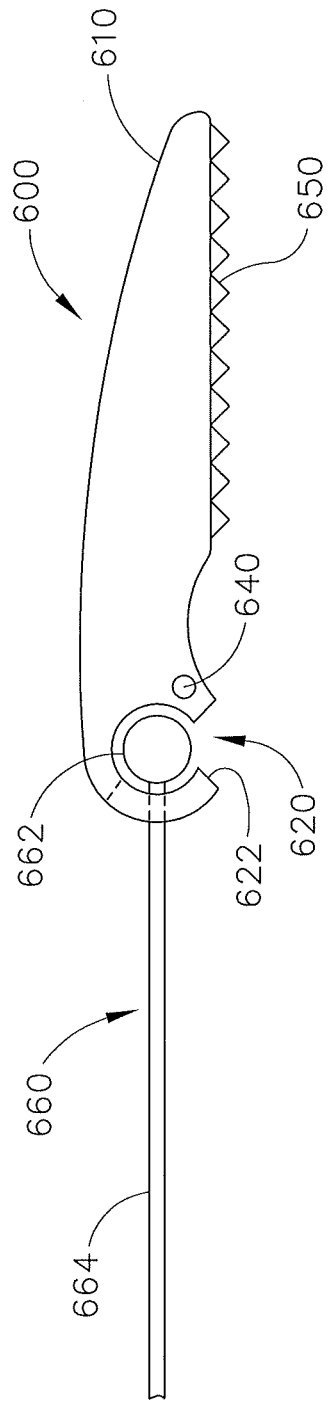
FIG. 9 depicts a side elevation view of the ball-snap clamp arm of FIG. 7 snapped onto a ball and rod actuator.

FIG. 7 depicts an exemplary ball-snap clamp arm (600) comprising a clamp body (610), a ball cup recess (620), a rod aperture (630), a pair of guide pins (640), and a clamp pad (650). In the present example, ball cup recess (620) is formed in a proximal end of clamp body (610) and is configured to receive a ball (662) of a ball rod (660) to actuate ball-snap clamp arm (600), shown in FIG. 9. Rod aperture (630), shown in FIG. 8, is formed through the proximal end of clamp body (610) and is configured to receive a rod (664) of ball rod (660) therethrough, but also to prevent ball (662) from longitudinally exiting ball cup recess (620). Clamp body (610) further includes detents (632) through which rod (664) may be snapped through to enter and remain within rod aperture (630). In present example, clamp body (610) also includes detents (622) about ball cup recess (620), such that ball (662) may be snapped into ball cup recess (620) as well. In some versions clamp body (610) comprises a resilient material to permit slight deformation of clamp body (610) to snap ball (662) and/or rod (664) into ball cup recess (620) and/or rod aperture (630). Accordingly, a user may couple and/or decouple ball-snap clamp arm (600) from a ball rod (660). Ball rod (660) is operable to actuate longitudinally relative to a shaft (670), shown in FIGS. 10A-10B. By way of example only, a trigger (not shown) of a handle assembly (not shown) may be pivoted to actuated ball rod (660). Clamp pad (650) is coupled to a lower surface of clamp body (610) and is operable to compress tissue against a blade (692), shown in FIGS. 10A-10B, when ball-snap clamp arm (600) is actuated to a closed position, shown in FIG. 10B. Clamp pad (650) may be constructed in accordance with at least some of the teachings of clamp pad (86, 220, 230, 344) described herein, in accordance with at least some of the teachings of U.S. Pat. Pub. No. 2006/0079874, and/or otherwise.

Referring now to FIGS. 10A-10B, guide pins (640) of the present example extend generally perpendicular to a longitudinal axis of ball-snap clamp arm (600) and are configured to slidably actuate within a slot (680) formed in a shaft (670). Shaft (670) extends distally from a handle assembly, such as handle assemblies (60, 380) described herein, and includes a pair of slots (680) formed on opposing sides of shaft (670). Slots (680) of the present example comprise linear slots formed at an angle relative to the longitudinal axis of shaft (670), though it should be understood that slots (680) may have other configurations, such as curved slots. Shaft (670) further includes an opening (not shown) on a distal end (672) through which ball-snap clamp arm (600) may be inserted and snapped onto ball rod (660) (shown in phantom). Shaft (670) may comprise a resilient material such that distal end (672) may deform to permit guide pins (640) to enter slots (680) when ball-snap clamp arm (600) is snapped onto ball rod (660). As shown in FIGS. 10A-10B, a waveguide (690) (shown in phantom) having a blade (692) extends longitudinally through shaft (670). Waveguide (690) and/or blade (692) of the present example may be configured in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757.

As shown in FIG. 10A, ball-snap clamp arm (600) is in an open position to permit tissue to enter between blade (692) and clamp pad (650). When ball rod (660) is actuated proximally, guide pins (640) slide within slots (680) and ball-snap clamp arm (600) is rotated relative to blade (692) to clamp tissue between ball-snap clamp arm (600) and blade (692). When ball-snap clamp arm (600) is in the closed position, shown in FIG. 10B, a transducer (not shown) may be activated to transmit oscillations along waveguide (690) to blade (692). When tissue is secured between blade (692) and ball-snap clamp arm (600), the ultrasonic oscillation of blade (692) may simultaneously sever tissue and denature the proteins in adjacent tissue cells, thereby providing a coagulative effect with relatively little thermal spread.

Once a user is finished with the surgical device, or if clamp pad (650) and/or ball-snap clamp arm (600) are worn out, the user unsnaps ball-snap clamp arm (600) from ball rod (660) and shaft (670). In the example shown, ball-snap clamp arm (600) is a disposable component and shaft (670), ball rod (660), waveguide (690), and blade (692) are reusable components. In some versions, only clamp pad (650) may be disposed of and the remainder of ball-snap clamp arm (600) may be cleaned and reused or reclaimed. In addition, the user may clean and reuse shaft (670), ball rod (660), waveguide (690), and blade (692) with a new ball-snap clamp arm (600). Still other arrangements for shaft (670), ball rod (660), waveguide (690), blade (692), and/or ball-snap clamp arm (600) will be apparent to one of ordinary skill in the art in view of the teachings herein.

C. Exemplary Living Hinge Clamp Arm

Figure 11:
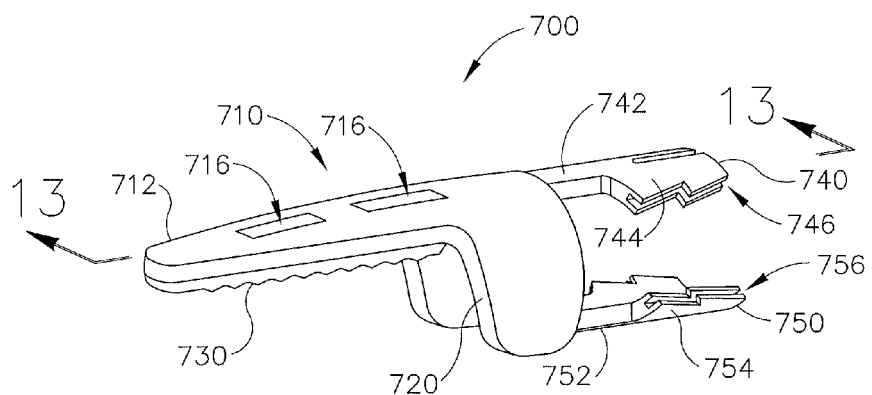
FIG. 11 depicts a perspective view of an exemplary clamp arm assembly having living hinges.
Figure 12:
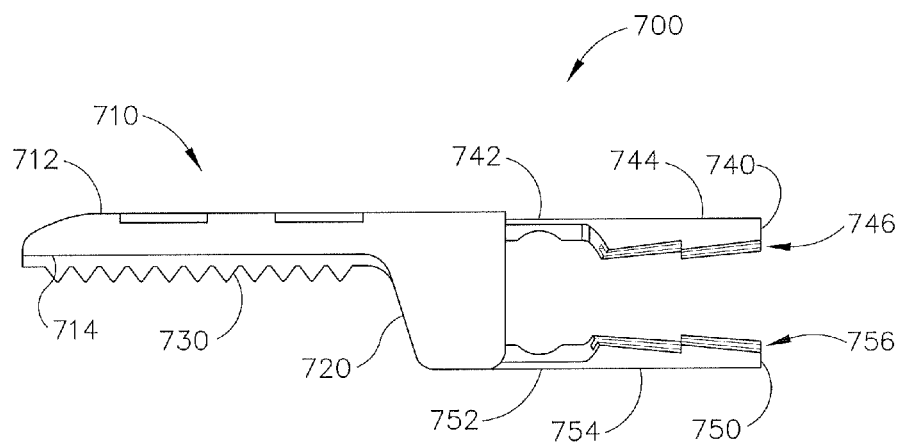
FIG. 12 depicts a side elevation view of the clamp arm assembly of FIG. 11.
Figure 13:
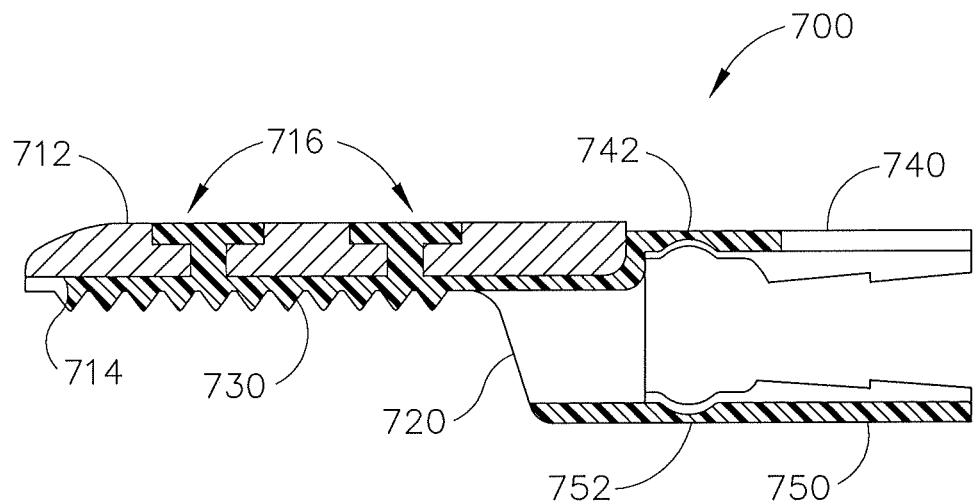
FIG. 13 depicts a side cross-sectional view of the clamp arm assembly of FIG. 11 taken along 13-13.

FIGS. 11-14 depict an exemplary alternative clamp arm (700) comprising a main body (710), a clamp pad (730), an upper living hinge member (740), and a lower living hinge member (750). Main body (710) of the present example comprises a clamp portion (712) and a hinge portion (720) proximal of the clamp portion (712). Referring to FIG. 13, clamp portion (712) comprises a substantially planar lower surface (714) and a pair of T-shaped mold locks (716). Lower surface (714) may optionally include surface features (not shown) to increase the adhesion of clamp pad (730), as will be discussed in more detail herein. Such surface features may include a ball-peen shot surface, a jagged surface, dimples, divots, and/or other surface features as will be apparent to one of ordinary skill in the art in view of the teachings herein. T-shaped mold locks (716) extend through an upper surface of clamp portion (712) to lower surface (714) such that an injected material may flow through T-shaped mold locks (716) from lower surface (714) to the upper surface. In the example shown, main body (710) includes a pair of T-shaped mold locks (716), but it should be understood that a single T-shaped mold lock (716) or more than two T-shaped mold locks (716) may be included. Furthermore, T-shaped mold locks (716) are not limited to a T-shape per se. Indeed, other geometric configurations will be apparent to one of ordinary skill in the art in view of the teachings herein, including cylindrical plugs, L-shapes, etc.

Hinge portion (720) is disposed proximally of clamp portion (712) and, in the present example, extends downwardly from clamp portion (712). By way of example only, hinge portion (720) presents a downwardly oriented C-shape relative to clamp portion (712). Each of the legs of the C shape further includes a channel (not shown) through which a fluid, such as injection mold material, may flow. The channels couple lower living hinge member (750) to clamp pad (730) via insert mold material that flows into and solidifies within the channels, as will be discussed in more detail below. In some versions main body (710) comprises a metallic material, though other materials may be used as well, including plastics, glass, etc. Main body (710) may be a first molded component prior to the insert molding of clamp pad (730) and/or living hinges (750). Still other modifications and/or configurations for main body (710) will be apparent to one of ordinary skill in the art in view of the teachings herein.

Clamp pad (730) of the present example is an insert molded piece that is molded onto main body (710). As shown in FIG. 13, when clamp pad (730) is molded onto main body (710), a portion of the mold material flows into T-shaped mold locks (716). When the injected material solidifies, clamp pad (730) and the material within T-shaped mold locks (716) form a single homogeneous continuum of material. Accordingly, the T-shaped material secures clamp pad (730) against main body (710), and the material within T-shaped mold locks (716) must be severed or broken to remove clamp pad (730) from main body (710). Clamp pad (730) may be further secured via the surface features of lower surface (714) described above. Of course, it should be understood that T-shaped mold locks (716) are merely optional, and clamp pad (730) may be coupled to main body (710) through other means, including adhesives, mechanical attachments (screws, staples, bolts, etc.), etc. In some versions clamp pad (730) comprises Teflon®, though other low-friction materials may be used as will be apparent to one of ordinary skill in the art in view of the teachings herein. Furthermore, clamp pad (730) may be constructed in accordance with at least some of the teachings of clamp pads (86, 220, 230, 344, 650) described herein and/or in accordance with at least some of the teachings of U.S. Pat. Pub. No. 2006/0079874, entitled "Tissue Pad for Use with an Ultrasonic Surgical Instrument," published Apr. 13, 2006, the disclosure of which is incorporated by reference herein; or may be omitted.

Figure 14:
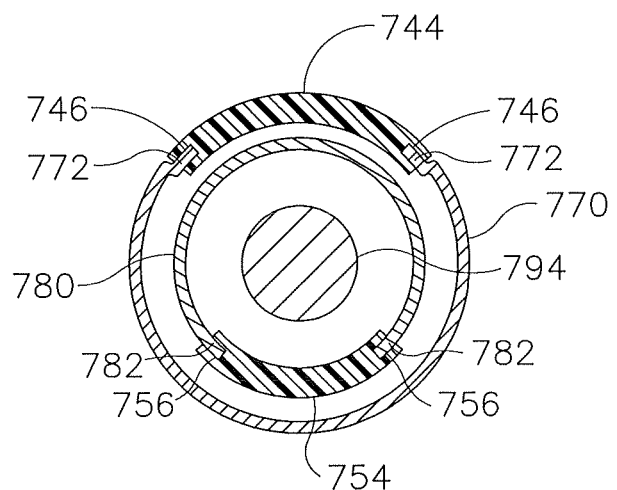
FIG. 14 depicts a front cross-sectional view of the clamp arm assembly of FIG. 11 showing the living hinges coupled to an outer sheath and an inner tubular actuation member.

As also shown in FIG. 13, upper living hinge member (740) of the present example extends proximally from clamp pad (730) and is unitarily formed with clamp pad (730) such that clamp pad (730) and upper hinge member (740) form a single homogeneous continuum of material. Upper hinge member (740) is an insert molded piece that is molded with clamp pad (730). Upper hinge member (740) is connected to clamp pad (730) via an upper living hinge (742) such that upper hinge member (740) may be pitched upwardly or downwardly relative to clamp pad (730) and/or main body (710). As shown in FIGS. 11-12 and 14, upper hinge member (740) comprises an arcuate member (744) having a pair of longitudinal upper slots (746) formed on opposing sides of upper hinge member (740). By way of example only, upper slots (746) extend longitudinally through the sides of arcuate member (744) such that arcuate ends (772) of an outer sheath (770), shown in FIG. 14, may be inserted into upper slots (746). When arcuate ends (772) are inserted into upper slots (746), upper hinge member (740) is coupled to outer sheath (770). Thus, main body (710) and/or clamp pad (730) may pivot relative to outer sheath (770) via living hinge (742). It should be understood that upper slots (746) may alternatively only partially extend through arcuate member (744) such that upper slots (746) terminate prior to the distal end of upper hinge member (740) at a distal wall. The distal wall may stop outer sheath (770) from extending out the distal end of upper hinge member (740), though this is merely optional.

In some versions, upper slots (746) may include snap features (not shown) to snap arcuate ends (772) into upper slots (746). Alternatively, a single slot may be formed longitudinally through a central portion of arcuate member (744) of upper hinge member (740). Accordingly, a portion of outer sheath (770) may be inserted into the single slot to couple outer sheath (770) to upper hinge member (740). Of course more than one slot may be formed through a central portion of arcuate member (744) as well. In other versions, a single slot may be formed at the proximal end of upper hinge member (740), and outer sheath (770) may be inserted into the end slot to couple outer sheath (770) to upper hinge member (740). Still further configurations for upper hinge member (740) will be apparent to one of ordinary skill in the art in view of the teachings herein.

Lower living hinge member (750) of the present example extends proximally from the bottom of hinge portion (720) of main body (710) and is unitarily formed with clamp pad (730) via the channels formed in hinge portion (720). Lower hinge member (750) is an insert molded piece that is molded with clamp pad (730). When the material for clamp pad (730) is injected into the mold, the material flows through and solidifies within the channels of hinge portion (720) such that lower living hinge member (750) and clamp pad (730) form a single homogeneous continuum of material. Lower hinge member (750) includes a lower living hinge (752) such that lower hinge member (750) may be pitched upwardly or downwardly relative to clamp pad (730) and/or main body (710). Of course it should be understood that lower living hinge member (750) may be a separately molded piece or, in some versions, lower living hinge member (750) may comprise two separate members each extending from a respective hinge portion (720). As shown in FIGS. 11-12 and 14, lower hinge member (750) comprises an arcuate member (754) having a pair of longitudinal lower slots (756) formed on opposing sides of lower hinge member (750). By way of example only, lower slots (756) extend longitudinally through the sides of arcuate member (754) such that arcuate ends (782) of an inner tubular actuation member (780), shown in FIG. 14, may be inserted into lower slots (756). When arcuate ends (782) are inserted into lower slots (756), lower hinge member (750) is coupled to inner tubular actuation member (780). Thus, main body (710) and/or clamp pad (730) may pivot relative to inner tubular actuation member (780) via living hinge (752). It should be understood that lower slots (756) may alternatively only partially extend through arcuate member (754) such that lower slots (756) terminate prior to the distal end of lower hinge member (750) at a distal wall. The distal wall may stop inner tubular actuation member (780) from extending out the distal end of lower hinge member (750), though this is merely optional.

In some versions, lower slots (756) may include snap features (not shown) to snap arcuate ends (782) into lower slots (756). Alternatively, a single slot may be formed longitudinally through a central portion of arcuate member (754) of lower hinge member (750). Accordingly, a portion of inner tubular actuation member (780) may be inserted into the single slot to couple inner tubular actuation member (780) to lower hinge member (750). Of course more than one slot may be formed through a central portion of arcuate member (754) as well. In other versions, a single slot may be formed at the proximal end of lower hinge member (750), and inner tubular actuation member (780) may be inserted into the end slot to couple inner tubular actuation member (780) to lower hinge member (750). Still further configurations for lower hinge member (750) will be apparent to one of ordinary skill in the art in view of the teachings herein.

Figure 15:
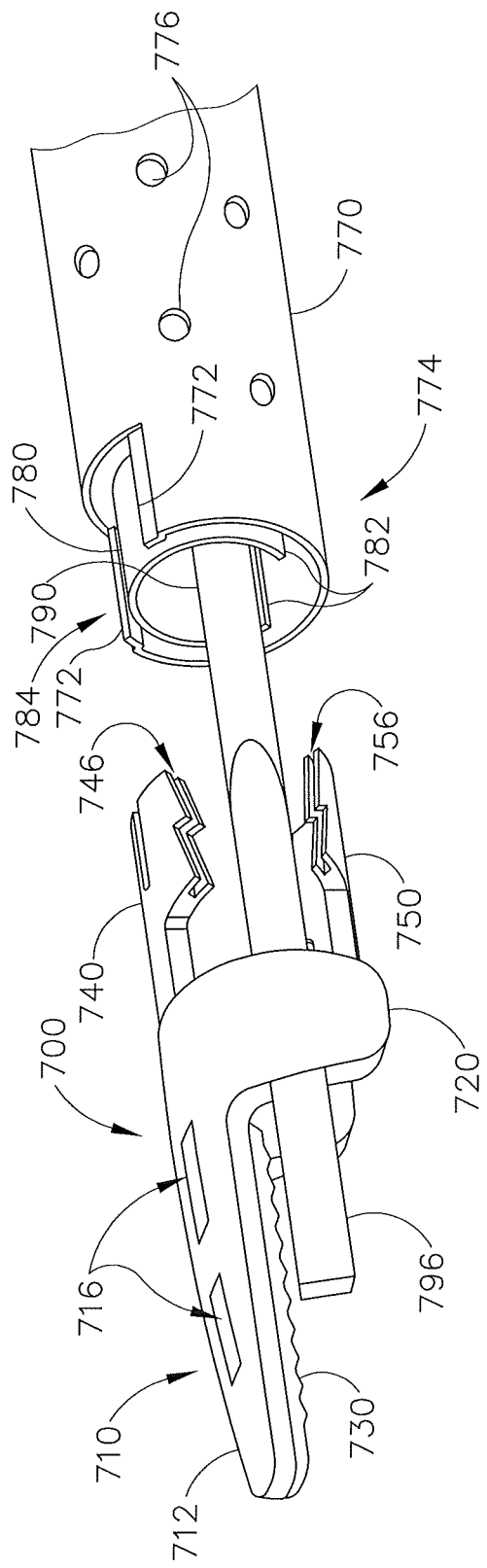
FIG. 15 depicts a perspective view of the clamp arm assembly of FIG. 11 aligned with an exemplary transmission assembly.

As shown in FIGS. 14-15, clamp arm (700) couples to a transmission assembly (760) comprising outer sheath (770), inner tubular actuation member (780), a waveguide (790), and a blade (794). Outer sheath (770) of the present example comprises an elongate tubular member having a proximal end (not shown) coupled to a handle assembly (not shown). The handle assembly may be constructed in accordance with at least some of the teachings of handle assemblies (60, 380) described herein or in accordance with at least some of the teachings of U.S. patent application Ser. No. 13/269,883, entitled "Surgical Instrument with Clutching Slip Ring Assembly to Power Ultrasonic Transducer," filed Oct. 10, 2011, now U.S. Pat. Pub. No. 2013/0090675, published Apr. 11, 2013; U.S. Pat. No. 8,998,939, entitled "Surgical Instrument with Modular End Effector," issued Apr. 7, 2015; U.S. Pat. Pub. No. 2012/0116263, entitled "Gear Driven Coupling Between Ultrasonic Transducer and Waveguide in Surgical Instrument," published May 10, 2012; U.S. Pat. Pub. No. 2012/0116262, entitled "Cam Driven Coupling Between Ultrasonic Transducer and Waveguide in Surgical Instrument," published May 10, 2012; U.S. patent application Ser. No. 13/269,870, entitled "Surgical Instrument with Modular Shaft and End Effector," filed Oct. 10, 2011, now U.S. Pat. Pub. No. 2012/0116388, published May 10, 2012; U.S. patent application Ser. No. 13/269,899, entitled "Ultrasonic Surgical Instrument with Modular End Effector," filed Oct. 10, 2011, now U.S. Pat. No. 9,050,125, issued Jun. 9, 2015; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757, the disclosures of which are herein incorporated by reference.

Outer sheath (770) has a distal end (774) having a notch cut out in an upper portion of outer sheath (770), as shown in FIG. 15. As a result, a pair of arcuate ends (772) are formed that are insertable into upper slots (746) as described above. FIG. 15 also shows outer sheath (770) comprising a plurality of holes (776) formed through the surface of outer sheath (770). Holes (776) permit fluid to enter into outer sheath (770) such that outer sheath (770) may be flushed with sterilization fluid to clean outer sheath (770). Of course holes (776) are merely optional, and other apertures may be used, including longitudinal slots, circumferential slots, mesh, etc. Moreover, outer sheath (770) may be constructed in accordance with the teachings of outer sheath (360) described above and/or otherwise, as will be apparent to one of ordinary skill in the art in view of the teachings herein.

Inner tubular actuation member (780) of the present example comprises an elongate tubular member disposed within outer sheath (770) and having a proximal end (not shown) coupled to a trigger of the handle assembly. The handle assembly and/or trigger may be constructed in accordance with at least some of the teachings of U.S. Pat. Pub. No.

2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461, 744; U.S. Pat. No. 6,500,176; U.S. Pat. Pub. No. 2011/ 0087218, now U.S. Pat. No. 8,939,974; and/or U.S. Pat. Pub. No. 2009/0143797, now U.S. Pat. No. 8,419,757. Inner tubular actuation member (780) has a distal end (784) having a notch cut out in an lower portion of inner tubular actuation member (780), as shown in FIG. 15. As a result, a pair of arcuate ends (782) are formed that are insertable into lower slots (756) as described above. Inner tubular actuation member (780) also comprises a plurality of holes (not shown) formed through the surface of inner tubular actuation member (780). The holes may be configured in accordance with at least some of the teachings of holes (776). For instance, the holes in inner tubular actuation member (780) permit fluid to enter into inner tubular actuation member (780) such that inner tubular actuation member (780) may be flushed with sterilization fluid to clean inner tubular actuation member (780). Of course the holes are merely optional, and other apertures may be used, including longitudinal slots, circumferential slots, mesh, etc. Inner tubular actuation member (780) may have other constructions, as will be apparent to one of ordinary skill in the art in view of the teachings herein.

Waveguide (790) comprises an elongate cylinder or tube coupled to a transducer (not shown) of the handle assembly. The transducer is operable to create linear oscillations or vibrations at an ultrasonic frequency (such as 55.5 kHz). With the transducer coupled to waveguide (790), these linear oscillations are transmitted through waveguide (790) to blade (794). The transducer may be constructed in accordance with at least some of the teachings of U.S. patent application Ser. No. 13/269,883, entitled "Surgical Instrument with Clutching Slip Ring Assembly to Power Ultrasonic Transducer," filed Oct. 10, 2011, now U.S. Pat. Pub. No. 2013/0090675, published Apr. 11, 2013; U.S. Pat. Pub. No. 2006/0079874; U.S. Pat. Pub. No. 2007/0191713; U.S. Pat. Pub. No. 2007/ 0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757. Waveguide (790) of the present example includes a threaded distal end (not shown) that threadably couples to a threaded proximal end of blade (794). The axial location of the threaded coupling of waveguide (790) to blade (794) may correspond to the last antinode of the ultrasonic oscillation produced by the transducer through waveguide (790), though this is merely optional. Blade (794) of the present example comprises a straight blade having a rectangular cuboid distal end operable to sever tissue when the transducer is activated. Blade (794) of the present example is a disposable blade such that the user may decouple blade (794) and couple a new blade (794) for a new procedure. Blade (794) may further be constructed in accordance with at least some of the teachings of blade (82) described above, in accordance with at least some of the teachings of U.S. Pat. Pub. No. 2006/0079874; U.S. Pat. Pub. No. 2007/ 0191713; U.S. Pat. Pub. No. 2007/0282333; U.S. Pat. Pub. No. 2008/0200940; U.S. Pat. Pub. No. 2011/0015660, now U.S. Pat. No. 8,461,744; and/or U.S. Pat. Pub. No. 2009/ 0143797, now U.S. Pat. No. 8,419,757, and/or otherwise.

In the example shown in FIG. 15, initially a user threadably couples blade (794) to waveguide (790). A user then couples upper hinge member (740) to outer sheath (770) and couples lower hinge member (750) to inner tubular actuation member (780). It should be understood that attachment of blade (794) to waveguide (790) may be performed after hinge member (740, 750) attachment. In some versions upper hinge member (740) slides onto outer sheath (770) and lower hinge member (750) slides onto inner tubular actuation member (780). In other versions, upper hinge member (740) snaps onto outer sheath (770) and lower hinge member (750) snaps onto inner tubular actuation member (780). For instance, one such merely exemplary snapping feature comprises an angled tab (not shown) formed on outer sheath (770) and an angled tab (not shown) formed on actuation member (780). These tabs are configured to snap into a respective hole (not shown) formed in upper hinge member (740) and in lower hinge member (750). Of course the tabs may be formed on upper hinge member (740) and lower hinge member (750) and the holes may be formed in outer sheath (770) and actuation member (780). Alternatively, the snap features may include pins that snap into holes formed at the ends of slots. Still other snap features will be apparent to one of ordinary skill in the art in view of the teachings herein. Such features for snapping upper hinge member (740) to outer sheath (770) and lower hinge member (750) to inner tubular actuation member (780) may be laser cut into outer sheath (770) and inner tubular actuation member (780). Alternatively, such features may be thixio-formed and welded to outer sheath (770) and/or tubular actuation member (780). Further still, such snap features may be screwed, snapped, clipped, clamped, adhesively attached, and/or otherwise secured to outer sheath (770) and/ or tubular actuation member (780).

Accordingly, with clamp arm (700) coupled to transmission assembly (760), when inner tubular actuation member (780) is actuated longitudinally via the trigger of the handle assembly and outer sheath (770) remains stationary, then clamp arm (700) is pivoted relative to blade (794). Thus, clamp arm (700) may be pivoted from an open position to a closed position to secure tissue between clamp pad (730) and blade (794). Accordingly, when the transducer is activated and tissue is secured between blade (794) and clamp arm (700), the ultrasonic oscillation of blade (794) may simultaneously sever tissue and denature the proteins in adjacent tissue cells, thereby providing a coagulative effect with relatively little thermal spread. Thus, a user may use clamp arm (700) coupled to outer sheath (770) and inner tubular actuation member (780) to clamp and sever tissue. When the user is finished with clamp arm (700), the user may detach and dispose of clamp arm (700). The user may then resterilize transmission assembly (760) and/or the handle assembly and attach a new clamp arm (700). In some versions, the user may send clamp arm (700) back to a manufacturer for reclamation. For instance, the manufacturer may initially cut away clamp pad (730), upper hinge (740), and lower hinge (750). The manufacturer may then resterilize main body (710) and mold a new clamp pad (730), upper hinge (740), and lower hinge (750) onto main body (710).

In some versions, inner tubular actuation member (780) remains stationary while outer sheath (770) is actuated. In still other versions, inner tubular actuation member (780) may be actuated distally while outer sheath (770) is actuated proximally, or vice-versa. Of course still other configurations for clamp arm (700), outer sheath (770), and/or inner tubular actuation member (780) will be apparent to one of ordinary skill in the art in view of the teachings herein.

D. Exemplary Pinned End Effector Assembly

Figure 16:
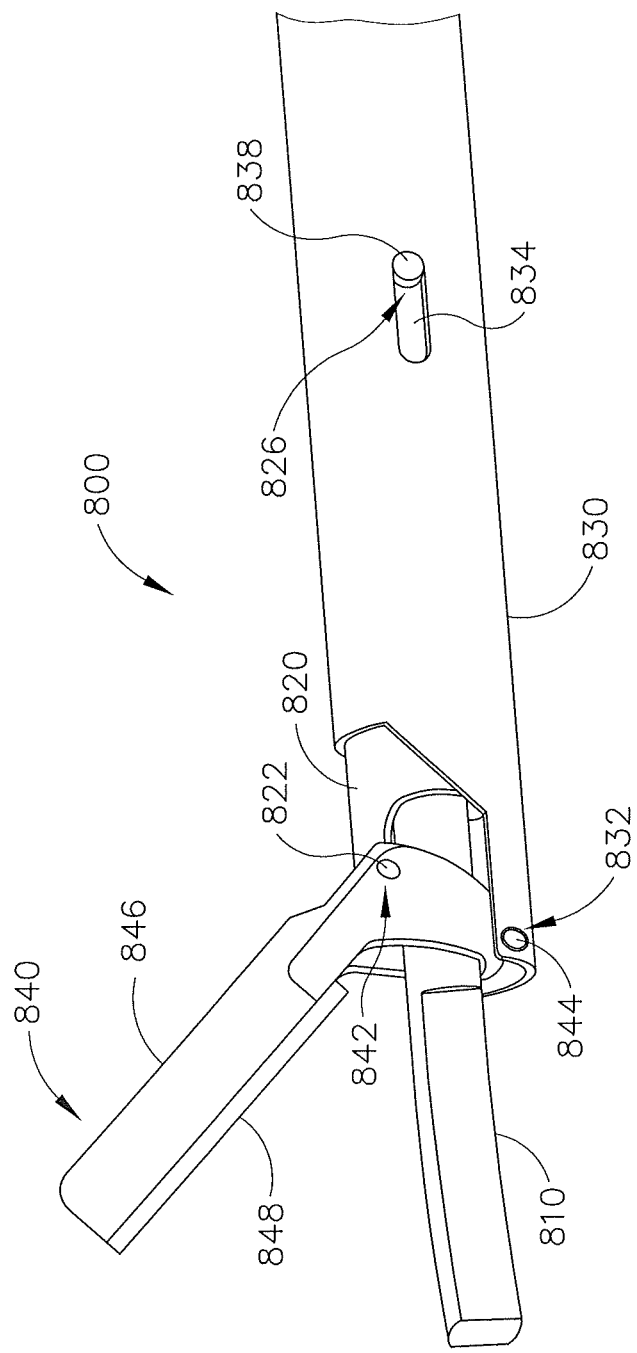
FIG. 16 depicts a perspective view of an exemplary pinned end effector assembly.
Figure 17:
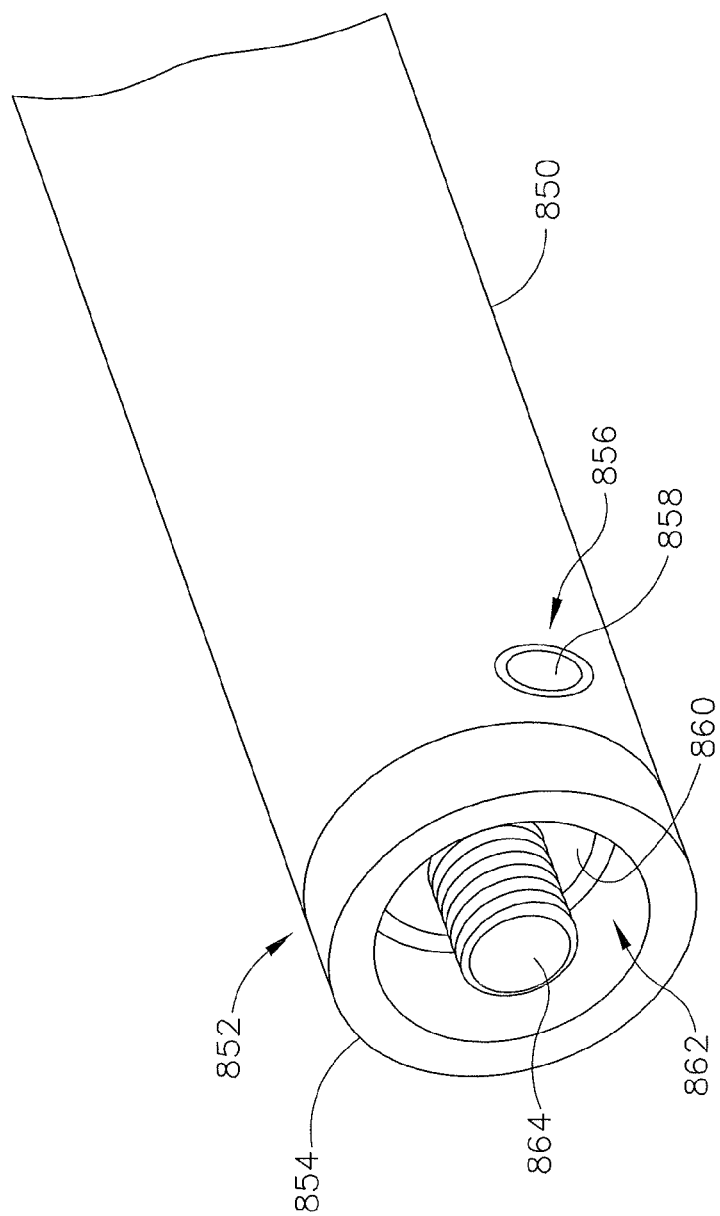
FIG. 17 depicts an enlarged perspective view of a distal end of an inner tube and waveguide.
Figure 18A:
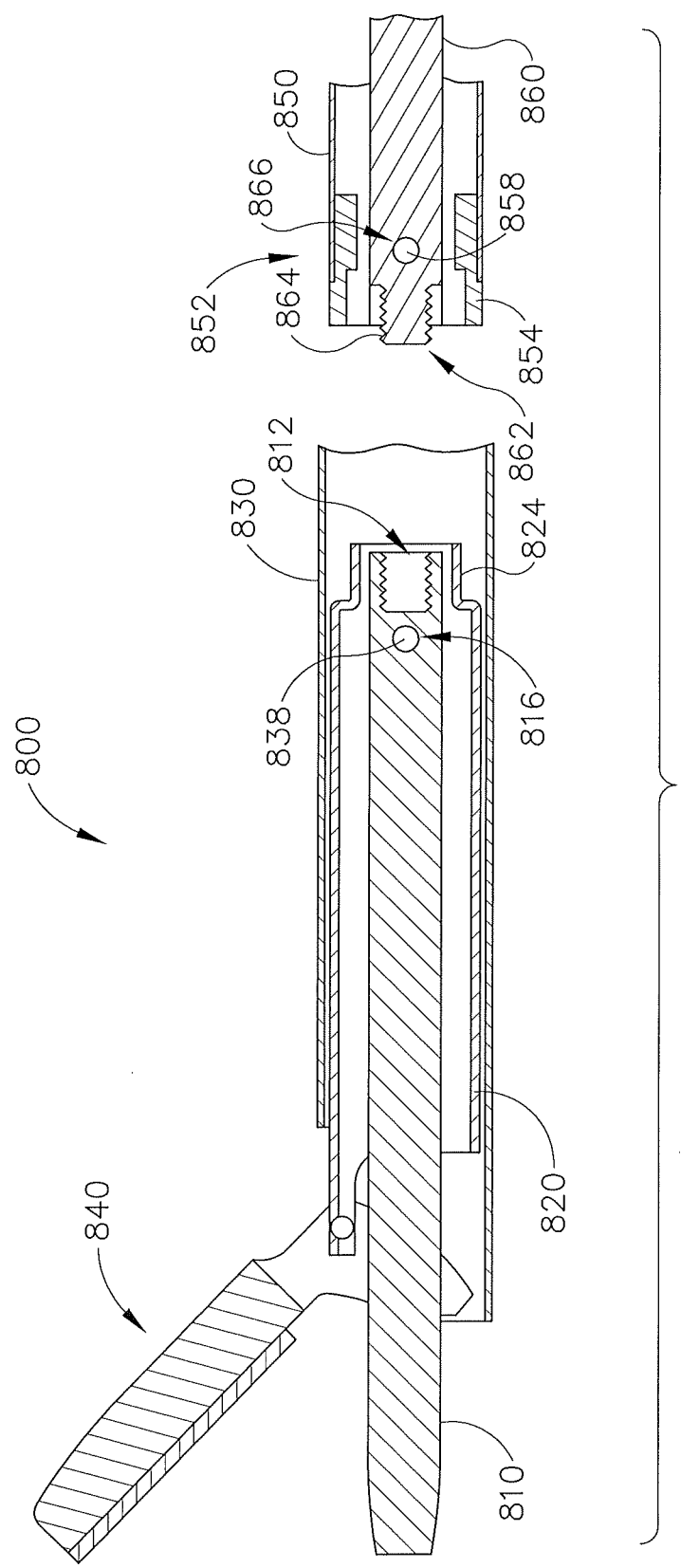
FIG. 18A depicts a side cross-sectional view showing the end effector assembly of FIG. 16 decoupled from the inner tube and waveguide of FIG. 17.
Figure 18B:
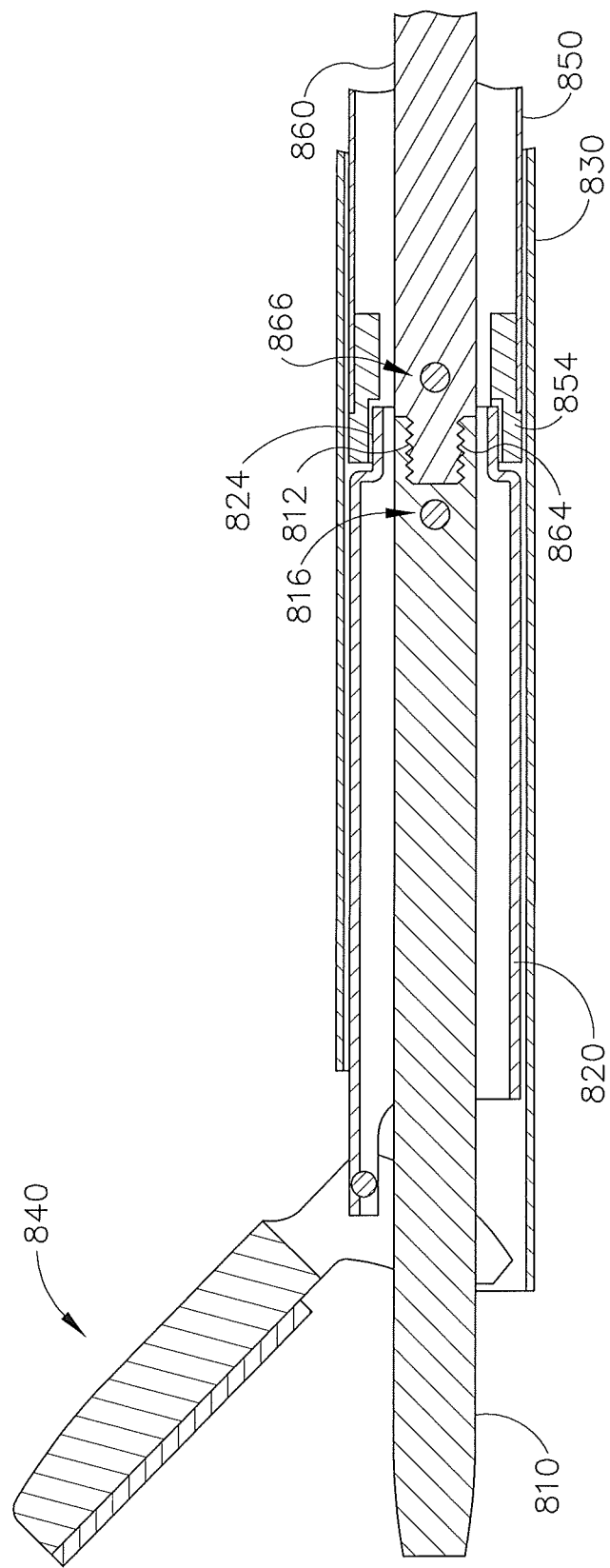
FIG. 18B depicts an enlarged side cross-sectional view of the end effector assembly, inner tube member, and waveguide of FIG. 18A shown coupled together.

FIGS. 16-18B depict an exemplary pinned end effector (800) for coupling to an inner tube (850) and a waveguide (860). As shown in FIG. 16, pinned end effector (800) comprises a blade (810), a distal inner tube portion (820), an outer sheath (830), and a clamp arm (840). Blade (810) comprises a metallic cylindrical rod having a rectangular cuboid distal end that is operable to sever tissue when coupled to waveguide (860) and a transducer is activated, as will be discussed in more detail below. Blade (810) may be further constructed in accordance with at least some of the teachings of blades (82, 794) described herein or in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; and/or U.S. Pat. Pub. No. 2009/0143797, now U.S. Pat. No. 8,419,757. Blade (810) of the present example further includes a threaded recess (812) at a proximal end, shown in FIGS. 18A-18B, that is configured to threadably couple to a threaded end (864) of waveguide (860). Also shown in FIGS. 18A-18B is a pin hole (816) formed through blade (810) such that pin hole (816) is perpendicular to a longitudinal axis of blade (810). Pin hole (816) is configured to receive a pin (838) therethrough. Still further configurations for blade (810) will be apparent to one of ordinary skill in the art in view of the teachings herein.

Distal inner tube portion (820) is coaxial to and disposed outside of blade (810). In the present example, distal inner tube portion (820) comprises a tubular member having an upper pin (822) at a distal end and an inwardly flared proximal end (824), shown in FIGS. 18A-18B. Upper pin (822) is configured to couple to clamp arm (840) at an upper pin hole (842) such that clamp arm (840) may be pivoted relative to distal inner tube portion (820). Inwardly flared proximal end (824) is configured to insert into a bushing (854) in communication with inner tube (850) and waveguide (860), as will be described in more detail herein. In some versions inwardly flared proximal end (824) is configured to form an interference fit with bushing (854), but this is merely optional. Distal inner tube portion (820) further includes a pin hole (826) coaxial to pin hole (816) such that a pin (838) may be inserted through pin hole (816) and the pin hole of distal inner tube portion (820) to couple blade (810) to distal inner tube portion (820). Of course other configurations for distal inner tube portion (820) will be apparent to one of ordinary skill in view of the teachings herein.

Still referring to FIG. 16, outer sheath (830) is coaxial to and disposed outside of distal inner tube portion (820) and blade (810). In the present example, outer sheath (830) comprises a tubular member having a lower pin hole (832) formed through a distal end of outer sheath (830). A proximal end of outer sheath (830) is configured to couple to a trigger in a handle assembly such that outer sheath (830) is longitudinally actuatable via the trigger. Merely exemplary constructions for handle assembly and/or trigger are disclosed in U.S. Pat. No. 8,998,939, entitled "Surgical Instrument with Modular End Effector," issued Apr. 7, 2015; U.S. Pat. Pub. No. 2012/0116263, entitled "Gear Driven Coupling Between Ultrasonic Transducer and Waveguide in Surgical Instrument," published May 10, 2012; U.S. Pat. Pub. No. 2012/0116262, entitled "Cam Driven Coupling Between Ultrasonic Transducer and Waveguide in Surgical Instrument," published May 10, 2012; U.S. patent application Ser. No. 13/269,870, entitled "Surgical Instrument with Modular Shaft and End Effector," filed Oct. 10, 2011, now U.S. Pat. Pub. No. 2012/0116388, published May 10, 2012; U.S. patent application Ser. No. 13/269,899, entitled "Ultrasonic Surgical Instrument with Modular End Effector," filed Oct. 10, 2011, now U.S. Pat. No. 9,050,125, issued Jun. 9, 2015; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757, the disclosures of which are herein incorporated by reference. Lower pin hole (832) is configured to receive a lower pin (844) of clamp arm (840) such that clamp arm (840) may be pivoted relative to blade (810) when outer sheath (830) is actuated longitudinally. Outer sheath (830) further includes a longitudinal slot (834) in which pin (838) may translate when outer sheath (830) is longitudinally actuated. As seen in FIG. 16, pin (838) is flush with the exterior surface of outer sheath (830) such that outer sheath (830), distal inner tube portion (820), and blade (810) are substantially secured relative to each other via pin (838), though it should be understood that slot (834) permits some longitudinal actuation of outer sheath (830) relative to pin (838). As with other components, other configurations for outer sheath (830) will be apparent to one of ordinary skill in the art in view of the teachings herein.

Clamp arm (840) of the present example comprises a body (846), having an upper pin hole (842) and lower pin (844), and a clamp pad (848). It the present example, clamp arm (840) is pivotable about upper pin (822) within upper pin hole (842) when outer sheath (830) actuates lower pin (844) distally and/or proximally. Accordingly, in the example shown in FIG. 16, outer sheath (830) is operable to pivot clamp arm (840) from an open position, when outer sheath (830) is actuated distally, to a closed position, when outer sheath (830) is actuated proximally. In some versions clamp arm (840) may be pivoted to the open position when outer sheath (830) is actuated proximally, and clamp arm (840) may be pivoted to the closed position when outer sheath (830) is actuated distally. When clamp arm (840) of the present example is in the closed position, clamp arm (840) and/or clamp pad (848) are compressed against blade (810). When clamp arm (840) is in the open position, clamp arm (840) and/or clamp pad (848) are opened at an angle relative to blade (810) such that tissue may be inserted between clamp arm (840) and blade (810). Clamp arm (840) may of course be further constructed in accordance with at least some of the teachings of clamp arms (84, 240, 320, 600, 700) disclosed herein and/or in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757. Still other configurations for clamp arm (840) will be apparent to one of ordinary skill in the art in view of the teachings herein.

Referring now to FIG. 17, inner tube (850) comprises a tubular member having a proximal end coupled to a handle assembly and a distal end (852) having a bushing (854) inserted therein. Inner tube (850) further includes a pin hole (856) that is perpendicular to the longitudinal axis of inner tube (850) and through which a second pin (858) is insertable. In some versions second pin (858) is welded to inner tube (850) once inserted through pin hole (856) in inner tube (850) and pin hole (866) of waveguide (860). In other versions, pin hole (856) may comprise a slot similar to slot (834) of outer sheath (830). Accordingly, second pin (858) may be permitted to actuate longitudinally relative to inner tube (850). Second pin (858) of the present example is also sized such that second pin (858) is flush with the exterior surface of inner tube (850) when inserted therein. Bushing (854) is in communication with the interior of distal end (852) of inner tube (850) and the exterior of distal end (862) of waveguide (860), thereby supporting distal end (862) of waveguide (860) within inner tube (850). Bushing (854) also includes a pin hole (not shown) that is coaxial to pin hole (856) such that second pin (858) is insertable therethrough. Of course other configurations for inner tube (850) and/or bushing (854) will be apparent to one of ordinary skill in the art in view of the teachings herein.

Waveguide (860) of the present example is coupled to a transducer at a proximal end of waveguide (860) and includes a threaded member (864) protruding from a distal end (862) of waveguide (860). The transducer may be constructed in accordance with at least some of the teachings of U.S. patent application Ser. No. 13/269,883, entitled "Surgical Instrument with Clutching Slip Ring Assembly to Power Ultrasonic Transducer," filed Oct. 10, 2011, now U.S. Pat. Pub. No. 2013/0090675, published Apr. 11, 2013; U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757, the disclosures of which are herein incorporated by reference. Threaded member (864) of the present example protrudes through bushing (854) and is configured to threadably couple to threaded recess (812) of blade (810). Accordingly, when waveguide (860) is coupled to blade (810), the oscillations produced by the transducer are transmitted through waveguide (860) to blade (810) such that blade (810) also oscillates at the ultrasonic frequency produced by the transducer. Waveguide (860) also includes a pin hole (866), shown in FIGS. 18A-18B, through which second pin (858) is inserted. Accordingly, second pin (858) couples inner tube (850), bushing (854), and waveguide (860) together and secures each relative to the others. In some versions, pins (838, 858) may be located at antinodes of the ultrasonic oscillation wave transmitted through waveguide (860), but this is merely optional. Indeed, pins (838, 858) may alternatively be located at nodes of the ultrasonic oscillation wave transmitted through waveguide (860). In still a further configuration, pin holes (816, 866) may be sized to permit translation of waveguide (860) and blade (810) relative to pin holes (816, 866) when ultrasonic oscillation waves are transmitted through waveguide (860) and blade (810). It should be understood that pins (838, 858) in this example still engage pin holes (816, 866) to thread blade (810) onto waveguide (860) when end effector (800) is rotated relative to inner tube (850) and waveguide (860). Other suitable configurations for waveguide (860) will be apparent to one of ordinary skill in the art in view of the teachings herein.

Referring now to FIGS. 18A-18B, when a user desires to couple end effector (800) to waveguide (860) and inner tube (850), the user initially inserts inner tube (850) and waveguide (860) into outer sheath (830). As end effector (800) is slid proximally onto inner tube (850), inwardly flared proximal end (824) of distal inner tube portion (820) inserts into bushing (854) of inner tube (850). In addition, threaded member (864) of waveguide (860) abuts threaded recess (812) of blade (810). The user then rotates end effector (800) until blade (810) is substantially acoustically coupled to waveguide (860) via threaded member (864) and threaded recess (812). It should be understood that pins (838, 858) need not be aligned. With blade (810) coupled to waveguide (860), outer sheath (830) is coupled to the trigger within the handle assembly. Merely exemplary coupling mechanisms for detachably coupling outer sheath (830) are disclosed in U.S. patent application Ser. No. 13/269,870, entitled "Surgical Instrument with Modular Shaft and End Effector," filed Oct. 10, 2011, now U.S. Pat. Pub. No. 2012/0116388, published May 10, 2012. With outer sheath (830) coupled to the trigger, the user may then use the surgical instrument to clamp and sever tissue using clamp arm (840) and blade (810). Once the user is finished with the surgical instrument, the user detaches outer sheath (830) and unthreads blade (810) from waveguide (860). The user may then dispose of the used end effector (800), resterilize inner tube (850), waveguide (860), and/or the handle assembly, and attach a new end effector (800) for use in another procedure.

E. Exemplary Slot and Resilient Tab Assembly

Figure 19A:
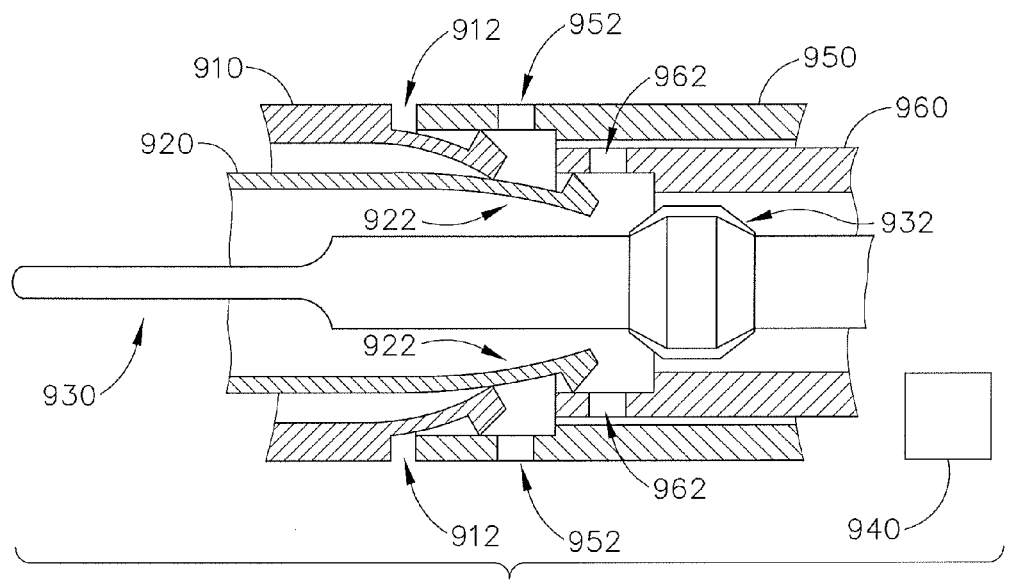
FIG. 19A depicts a side cross-sectional view of a slot and resilient tab assembly for an outer sheath and an inner tubular actuation member shown in an open position.
Figure 19B:
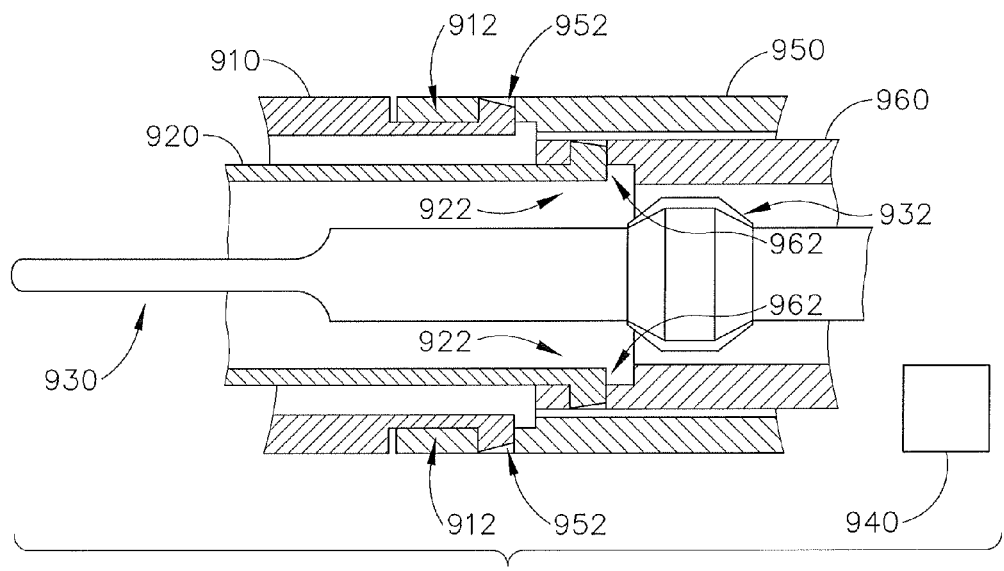
FIG. 19B depicts the slot and resilient tab assembly of FIG. 19A shown in a closed position.

FIGS. 19A-19B depict an exemplary alternative clamp arm coupling for coupling a distal outer sheath (910) and a distal inner tube (920) of an end effector (not shown) to an outer sheath (950) and an inner tube (960). Distal outer sheath (910) of the present example comprises a tubular member having a pair of resilient tabs (912) at a proximal end and configured to snap into a pair of outer sheath slots (952) formed in a distal end of outer sheath (950). Distal inner tube (920) comprises a tubular member also having a pair of resilient tabs (922) at a proximal end and configured to snap into a pair of inner tube slots (962) formed in a distal end of inner tube (960). Distal outer sheath (910) and distal inner tube (920) are coupled to a clamp arm (not shown) at a distal end of each such that clamp arm is pivotable relative to a blade (930) via longitudinal actuation of distal outer sheath (910) and/or distal inner tube (920). For instance, distal outer sheath (910), distal inner tube (920), and/or the clamp arm may be constructed in accordance with at least some of the teachings of end effector (800), clamp arm (700), transmission assembly (760), clamp arm (600), clamp arm assembly (400), transmission assembly (450), clamp arm assembly (300), transmission assembly (350), end effector (200), end effector (80), and/or in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660, now U.S. Pat. No. 8,461,744; U.S. Pat. No. 6,500,176; U.S. Pat. Pub. No. 2011/0087218, now U.S. Pat. No. 8,939,974; and/or U.S. Pat. Pub. No. 2009/0143797, now U.S. Pat. No. 8,419,757.

Outer sheath (950) comprises a tubular member having a pair of outer sheath slots (952) at a distal end that are configured to receive resilient tabs (912) therein. The proximal end of outer sheath (950) is coupled to a handle assembly (not shown). In some versions outer sheath (950) is actuatable via a trigger (not shown) of the handle assembly. In other versions outer sheath (950) is fixedly coupled to the handle assembly. Inner tube (960) comprises a tubular member having a pair of inner tube slots (962) at a distal end that are configured to receive resilient tabs (922) therein. The proximal end of inner tube (960) is also coupled to the handle assembly. In some versions inner tube (960) is actuatable via the trigger of the handle assembly. In other versions inner tube (960) is fixedly coupled to the handle assembly. In the present example, the handle assembly includes an actuator (940) operable to actuate both outer sheath (950) and inner tube (960) distally relative to blade (930). For instance, FIG. 19B depicts outer sheath (950) and inner tube (960) shown in a closed position prior to actuation by actuator (940). When actuator (940) is activated by a user, outer sheath (950) and inner tube (960) translate distally relative to the handle assembly and blade (930) as shown in FIG. 19A. In some versions actuator (940) comprises a slider operable to extend outer sheath (950) and inner tube (960) distally relative to blade (930) and the handle assembly. In other versions actuator (940) comprises a push button operable to actuate outer sheath (950) and inner tube (960) distally relative to blade (930) and the handle assembly. Of course still other configurations for outer sheath (950), inner tube (960), and actuator (940) will be apparent to one of ordinary skill in the art in view of the teachings herein.

Blade (930) of the present example is selectively coupleable to a waveguide (not shown) and is operable to sever tissue. In the example shown in FIGS. 19A-19B, blade (930) comprises a connector (932) configured to selectively couple to the waveguide. Merely exemplary configurations for connector (932) include threading, a leur lock, bayonet fittings, snaps, etc. In some versions, connector (932) is longitudinally positioned to correspond to the distal-most node of blade (930). The waveguide is coupled to a transducer, such as transducer (100) described herein, such that ultrasonic oscillations are transmitted to the waveguide. When blade (930) is coupled to waveguide, blade (930) also oscillates ultrasonically to simultaneously sever tissue and denature the proteins in adjacent tissue cells, thereby providing a coagulative effect with relatively little thermal spread.

When a user desires to couple distal outer sheath (910) to outer sheath (950) and distal inner tube (920) to inner tube (960), initially the user uses actuator (940) to extend outer sheath (950) and inner tube (960) distally relative to blade (930). As shown in FIG. 19A, when outer sheath (950) and inner tube (960) are extended distally, the user inserts resilient tabs (912) of distal outer sheath (910) into outer sheath slots (952) and resilient tabs (922) of distal inner tube (920) into inner tube slots (962). With tabs (912, 922) inserted into slots (952, 962), the user uses actuator (940) such that outer sheath (950) and inner tube (960) retract proximally relative to blade (930). As will be apparent to one of ordinary skill in the art, distal outer sheath (910) and distal inner tube (920) also retract proximally as a result of the coupling of tabs (912, 922) with slots (952, 962). As shown in FIG. 19B, actuator (940) is configured to retract outer sheath (950) and inner tube (960) such that the connections of tabs (912, 922) and slots (952, 962) overlap, thereby substantially preventing tab (912) from disengaging from slot (952). In addition, actuator (940) is configured to retract inner tube (960) such that the connection of tab (922) and slot (962) is longitudinally aligned with connector (932). Connector (932) of the present example is sized and configured to substantially prevent tab (922) from disengaging from slot (962). In some versions, connector (932) may include a seal (not shown) disposed about the circumference of connector (932) and configured to substantially fluidly seal connector (932) to the interior of inner tube (960) and/or distal inner tube (920). With outer sheath (950) coupled to distal outer sheath (910) and inner tube (960) coupled to distal inner tube (920), the user may then use the surgical instrument. When the user is finished with the instrument, distal outer sheath (910) and distal inner tube (920) are disengaged and the end effector may be disposed of. In some versions blade (930) may be decoupled and disposed of as well. The user may then clean the surgical instrument, including outer sheath (950) and inner tube (960), and then couple a new end effector having a distal outer sheath (910) and distal inner tube (920) for use in a new procedure.

In some versions distal outer sheath (910) and outer sheath (950) comprise a rotatable coupling, such as a bayonet and slot, a leur lock, etc. Distal inner tube (920) and inner tube (960) may also comprise a rotatable coupling, such as a bayonet and slot, a leur lock, etc. One or more indicators (not shown) may be provided on distal outer sheath (910), outer sheath (950), distal inner tube (920), and/or inner tube (960) to indicate an initial insertion position and/or a locked position for the rotatable coupling. To couple distal outer sheath (910) to outer sheath (950) and distal inner tube (920) to inner tube (960), the user uses actuator (940) to extend outer sheath (950) and inner tube (960) distally relative to blade (930). The user then inserts distal outer sheath (910) and distal inner tube (920) into the receiving portion of the rotatable coupling and rotates distal outer sheath (910) and distal inner tube (920) to engage the rotatable coupling. The user then uses actuator (940) to retract outer sheath (950) and inner tube (960) to the closed position to use the surgical instrument. When the user is finished with the instrument, distal outer sheath (910) and distal inner tube (920) are disengaged and the end effector may be disposed of. In some versions blade (930) may be decoupled and disposed of as well. The user may then clean the surgical instrument, including outer sheath (950) and inner tube (960), and then couple a new end effector having a distal outer sheath (910) and distal inner tube (920) for use in a new procedure.

As with other components described herein, distal outer sheath (910), distal inner tube (920), blade (930), actuator (940), outer sheath (950), and/or inner tube (960) may have other configurations as will be apparent to one of ordinary skill in the art in view of the teachings herein. Indeed, in some versions distal outer sheath (910) and outer sheath (950) may be omitted. In other versions, distal inner tube (920) and inner tube (960) may be omitted.

While certain configurations of exemplary surgical instruments have been described, various other ways in which the surgical instruments may be configured will be apparent to those of ordinary skill in the art in view of the teachings herein. By way of example only, the surgical instruments referred to herein may be constructed in accordance with at least some of the teachings of U.S. Pat. No. 6,500,176; U.S. Pat. No. 6,783,524; U.S. Pat. No. 7,416,101; U.S. Pat. No. 7,738,971; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0209990, now U.S. Pat. No. 8,657,174; U.S. Pub. No. 2009/0143797, now U.S. Pat. No. 8,419,757; U.S. Pub. No. 2010/0069940, now U.S. Pat. No. 9,023,071; and/or U.S. Provisional Application Ser. No. 61/410,603.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, the surgical instrument comprising:
   (a) a body assembly;
   (b) a transmission assembly extending distally from the body assembly, the transmission assembly comprising:
      (i) an ultrasonic blade,
      (ii) an inner member, wherein the inner member defines a longitudinal axis, and
      (iii) an outer sheath disposed about at least a portion of the inner member; and
   (c) a clamp arm assembly selectively coupled to the transmission assembly and comprising a clamp arm, wherein the clamp arm is operable to pivot relative to the ultrasonic blade between a loading position, an open position, and a closed position, wherein the clamp arm is configured to extend obliquely relative to the longitudinal axis of the inner member when in the loading position, wherein the clamp arm is configured to selectively engage the inner member or the outer sheath in the loading position;
   wherein at least one of the inner member or the outer sheath is configured to actuate longitudinally between a distal position, an intermediate position, and a proximal position, wherein the loading position of the clamp arm correlates with the distal position, the open position of the clamp arm correlates with the intermediate position, and the closed position of the clamp arm correlates with the proximal position.

2. The surgical instrument of claim 1 wherein the clamp arm assembly further comprises an outer sheath portion, wherein the outer sheath portion is configured to selectively couple to the outer sheath of the transmission assembly.

3. The surgical instrument of claim 2, wherein the outer sheath portion comprises threading, wherein the outer sheath comprises complementary threading, wherein the outer sheath portion threadably couples to the outer sheath.

4. The surgical instrument of claim 2, wherein the outer sheath portion comprises a bayonet, wherein the outer sheath comprises a slot.

5. The surgical instrument of claim 2, wherein the inner member is coupled to a user input feature.

6. The surgical instrument of claim 5 wherein the user input feature is operable to actuate the inner member between the distal position, the intermediate position, and the proximal position.

7. An ultrasonic surgical instrument, the surgical instrument comprising:
   (a) a body assembly;
   (b) a transmission assembly extending distally from the body assembly, the transmission assembly comprising:
      (i) an ultrasonic blade,
      (ii) an inner member, wherein the inner member defines a slot, and
      (iii) an outer sheath disposed about at least a portion of the inner member; and
   (c) a clamp arm assembly selectively coupled to the transmission assembly and comprising a clamp arm, wherein the clamp arm is operable to pivot relative to the ultrasonic blade, wherein the clamp arm comprises a tubular member configured to receive the ultrasonic blade, wherein the clamp arm further comprises a tab extending downwardly from the tubular member of the clamp arm from a position below the ultrasonic blade, wherein the tab extends through the slot of the inner member to thereby selectively couple the clamp arm to the inner member;
   wherein at least one of the inner member or the outer sheath is configured to actuate longitudinally.

* * * * *